(12) United States Patent
Shelton, IV et al.

(10) Patent No.: US 7,673,780 B2
(45) Date of Patent: Mar. 9, 2010

(54) ARTICULATION JOINT WITH IMPROVED MOMENT ARM EXTENSION FOR ARTICULATING AN END EFFECTOR OF A SURGICAL INSTRUMENT

(75) Inventors: Frederick E. Shelton, IV, Hillsboro, OH (US); Jeffrey S. Swayze, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1146 days.

(21) Appl. No.: 11/270,305

(22) Filed: Nov. 9, 2005

(65) Prior Publication Data

US 2007/0102474 A1 May 10, 2007

(51) Int. Cl.
*A61B 17/068* (2006.01)
*F16L 27/02* (2006.01)

(52) U.S. Cl. .................. 227/175.1; 227/181.1; 285/184

(58) Field of Classification Search .............. 227/175.1, 227/181.1; 285/184
See application file for complete search history.

(56) References Cited

U.S. PATENT DOCUMENTS

| | | | |
|---|---|---|---|
| 2,037,727 A | | 4/1936 | Chapelle |
| 3,894,174 A | | 7/1975 | Cartun |
| 3,940,844 A | | 3/1976 | Colby et al. |
| 4,180,285 A | * | 12/1979 | Reneau ........................ 285/261 |
| 4,520,817 A | | 6/1985 | Green |
| 4,526,174 A | | 7/1985 | Froehlich |
| 4,540,202 A | * | 9/1985 | Amphoux et al. ........... 285/184 |
| 4,566,620 A | * | 1/1986 | Green et al. .................. 227/19 |
| 4,573,622 A | * | 3/1986 | Green et al. .................. 227/19 |
| 4,606,343 A | | 8/1986 | Conta et al. |
| 4,709,120 A | | 11/1987 | Pearson |
| 4,809,695 A | | 3/1989 | Gwathmey et al. |
| 4,860,644 A | * | 8/1989 | Kohl et al. .................... 454/65 |
| 4,892,244 A | | 1/1990 | Fox et al. |
| 4,941,623 A | | 7/1990 | Pruitt |
| 4,955,959 A | | 9/1990 | Tompkins et al. |
| 5,027,834 A | | 7/1991 | Pruitt |
| 5,031,814 A | | 7/1991 | Tompkins et al. |

(Continued)

FOREIGN PATENT DOCUMENTS

CA     2458946 A1     3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner*—Rinaldi I. Rada
*Assistant Examiner*—Gloria R. Weeks
(74) *Attorney, Agent, or Firm*—Dean Garner

(57) ABSTRACT

An articulation joint for use in connection with a surgical instrument that has a portion that must be passed through a trocar or similar structure and then articulated relative to another portion of the instrument received within the trocar. Various embodiments of the articulation joint provide structures for increasing the moment arm between the actuator and the pivot point between the proximal and distal tube segments interconnecting a handle assembly of the surgical instrument to a surgical implement such as an end effector of an endocutter.

4 Claims, 15 Drawing Sheets

U.S. PATENT DOCUMENTS

| | | | |
|---|---|---|---|
| 5,040,715 A | 8/1991 | Green et al. |
| 5,080,556 A | 1/1992 | Carreno |
| 5,106,008 A | 4/1992 | Tompkins et al. |
| 5,111,987 A | 5/1992 | Moeinzadeh et al. |
| 5,129,570 A | 7/1992 | Schulze et al. |
| 5,156,315 A | 10/1992 | Green et al. |
| 5,211,649 A | 5/1993 | Kohler et al. |
| 5,246,156 A | 9/1993 | Rothfuss et al. |
| 5,253,793 A | 10/1993 | Green et al. |
| RE34,519 E | 1/1994 | Fox et al. |
| 5,275,323 A | 1/1994 | Schulze et al. |
| 5,307,976 A | 5/1994 | Olson et al. |
| 5,318,221 A | 6/1994 | Green et al. |
| 5,336,130 A * | 8/1994 | Ray ............................ 454/65 |
| 5,348,259 A * | 9/1994 | Blanco et al. ............ 248/276.1 |
| 5,350,400 A | 9/1994 | Esposito et al. |
| 5,379,933 A | 1/1995 | Green et al. |
| 5,383,880 A | 1/1995 | Hooven |
| 5,395,033 A | 3/1995 | Byrne et al. |
| 5,397,046 A | 3/1995 | Savage et al. |
| 5,403,312 A | 4/1995 | Yates et al. |
| 5,413,267 A | 5/1995 | Solyntjes et al. |
| 5,413,268 A | 5/1995 | Green et al. |
| 5,415,335 A | 5/1995 | Knodell, Jr. |
| 5,425,745 A | 6/1995 | Green et al. |
| 5,431,322 A | 7/1995 | Green et al. |
| 5,433,721 A | 7/1995 | Hooven et al. |
| 5,445,304 A | 8/1995 | Plyley et al. |
| 5,456,401 A | 10/1995 | Green et al. |
| 5,462,215 A | 10/1995 | Viola et al. |
| 5,465,895 A | 11/1995 | Knodel et al. |
| 5,465,896 A | 11/1995 | Allen et al. |
| 5,470,006 A | 11/1995 | Rodak |
| 5,472,132 A | 12/1995 | Savage et al. |
| 5,474,566 A | 12/1995 | Alesi et al. |
| 5,480,089 A | 1/1996 | Blewett |
| 5,482,197 A | 1/1996 | Green et al. |
| 5,485,947 A | 1/1996 | Olson et al. |
| 5,497,933 A | 3/1996 | DeFonzo et al. |
| 5,518,164 A | 5/1996 | Hooven |
| 5,529,235 A | 6/1996 | Boiarski et al. |
| 5,535,934 A | 7/1996 | Boiarski et al. |
| 5,564,615 A | 10/1996 | Bishop et al. |
| 5,577,654 A | 11/1996 | Bishop |
| 5,588,579 A | 12/1996 | Schnut et al. |
| 5,601,224 A | 2/1997 | Bishop et al. |
| 5,607,094 A | 3/1997 | Clark et al. |
| 5,609,285 A * | 3/1997 | Grant et al. .............. 227/179.1 |
| 5,630,539 A | 5/1997 | Plyley et al. |
| 5,639,008 A | 6/1997 | Gallagher et al. |
| 5,653,373 A | 8/1997 | Green et al. |
| 5,673,840 A | 10/1997 | Schulze et al. |
| 5,673,841 A | 10/1997 | Schulze et al. |
| 5,680,983 A | 10/1997 | Plyley et al. |
| 5,688,270 A | 11/1997 | Yates et al. |
| 5,692,668 A | 12/1997 | Schulze et al. |
| 5,702,408 A | 12/1997 | Wales et al. |
| 5,704,534 A | 1/1998 | Huitema et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,743,456 A * | 4/1998 | Jones et al. .............. 227/176.1 |
| 5,762,256 A | 6/1998 | Mastri et al. |
| 5,779,130 A | 7/1998 | Alesi et al. |
| 5,782,396 A | 7/1998 | Mastri et al. |
| 5,791,231 A | 8/1998 | Cohn et al. |
| 5,797,536 A | 8/1998 | Smith et al. |
| 5,797,537 A | 8/1998 | Oberlin et al. |
| 5,797,538 A | 8/1998 | Heaton et al. |
| 5,823,066 A | 10/1998 | Huitema et al. |
| 5,826,776 A | 10/1998 | Schulze et al. |
| 5,833,690 A | 11/1998 | Yates et al. |
| 5,836,503 A | 11/1998 | Ehrenfels et al. |
| 5,839,639 A | 11/1998 | Sauer et al. |
| 5,865,361 A | 2/1999 | Milliman et al. |
| 5,878,938 A | 3/1999 | Bittner et al. |
| 5,893,506 A | 4/1999 | Powell |
| 5,894,979 A | 4/1999 | Powell |
| 5,901,895 A * | 5/1999 | Heaton et al. ............ 227/176.1 |
| 5,911,353 A | 6/1999 | Bolanos et al. |
| 5,918,791 A | 7/1999 | Sorrentino et al. |
| 5,941,442 A | 8/1999 | Geiste et al. |
| 5,954,259 A | 9/1999 | Viola et al. |
| 5,988,479 A | 11/1999 | Palmer |
| 6,010,054 A | 1/2000 | Johnson et al. |
| 6,017,356 A | 1/2000 | Frederick et al. |
| 6,022,352 A | 2/2000 | Vandewalle |
| 6,032,849 A | 3/2000 | Mastri et al. |
| 6,079,606 A | 6/2000 | Milliman et al. |
| 6,083,234 A | 7/2000 | Nicholas et al. |
| 6,109,500 A | 8/2000 | Alli et al. |
| H1904 H | 10/2000 | Yates et al. |
| 6,131,789 A | 10/2000 | Schulze et al. |
| 6,155,473 A | 12/2000 | Tompkins et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,087 B1 | 7/2001 | Whitman |
| 6,315,184 B1 | 11/2001 | Whitman |
| 6,320,123 B1 | 11/2001 | Reimers |
| 6,358,224 B1 | 3/2002 | Tims et al. |
| 6,416,486 B1 | 7/2002 | Wampler |
| 6,443,973 B1 | 9/2002 | Whitman |
| 6,488,197 B1 | 12/2002 | Whitman |
| 6,491,201 B1 | 12/2002 | Whitman |
| 6,503,139 B2 * | 1/2003 | Coral ........................ 454/65 |
| 6,522,101 B2 | 2/2003 | Malackowski |
| 6,524,180 B1 * | 2/2003 | Simms et al. ................. 454/65 |
| 6,619,529 B2 | 9/2003 | Green et al. |
| 6,629,988 B2 | 10/2003 | Weadock |
| 6,644,532 B2 | 11/2003 | Green et al. |
| 6,669,073 B2 | 12/2003 | Milliman et al. |
| 6,681,979 B2 | 1/2004 | Whitman |
| 6,695,199 B2 | 2/2004 | Whitman |
| 6,716,233 B1 | 4/2004 | Whitman |
| 6,723,087 B2 | 4/2004 | O'Neill et al. |
| 6,755,338 B2 | 6/2004 | Hahnen et al. |
| 6,773,438 B1 | 8/2004 | Knodel et al. |
| 6,786,382 B1 | 9/2004 | Hoffman |
| 6,793,652 B1 | 9/2004 | Whitman et al. |
| 6,817,509 B2 | 11/2004 | Geiste et al. |
| 6,830,174 B2 | 12/2004 | Hillstead et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,913,613 B2 | 7/2005 | Schwarz et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,032,798 B2 | 4/2006 | Whitman et al. |

| | | | | | | |
|---|---|---|---|---|---|---|
| 7,032,799 B2 | 4/2006 | Viola et al. | | 2007/0106317 A1 | 5/2007 | Shelton, IV et al. |
| 7,044,352 B2 | 5/2006 | Shelton, IV et al. | | 2007/0114261 A1 | 5/2007 | Ortiz et al. |
| 7,055,730 B2 | 6/2006 | Ehrenfels et al. | | 2007/0158385 A1 | 7/2007 | Hueil et al. |
| 7,055,731 B2 | 6/2006 | Shelton, IV et al. | | 2007/0170225 A1 | 7/2007 | Shelton, IV et al. |
| 7,066,944 B2 | 6/2006 | Laufer et al. | | 2007/0175949 A1 | 8/2007 | Shelton, IV et al. |
| 7,083,075 B2 | 8/2006 | Swayze et al. | | 2007/0175950 A1 | 8/2007 | Shelton, IV et al. |
| 7,140,527 B2 | 11/2006 | Ehrenfels et al. | | 2007/0175951 A1 | 8/2007 | Shelton, IV et al. |
| 7,246,734 B2 | 7/2007 | Shelton, IV | | 2007/0175953 A1 | 8/2007 | Shelton, IV et al. |
| 7,303,106 B2 | 12/2007 | Milliman et al. | | 2007/0175955 A1 | 8/2007 | Shelton, IV et al. |
| 7,328,828 B2 | 2/2008 | Ortiz et al. | | 2007/0175956 A1 | 8/2007 | Swayze et al. |
| 7,354,447 B2 | 4/2008 | Shelton, IV et al. | | 2007/0175957 A1 | 8/2007 | Shelton, IV et al. |
| 7,380,695 B2 | 6/2008 | Doll et al. | | 2007/0175958 A1 | 8/2007 | Shelton, IV et al. |
| 7,404,508 B2 | 7/2008 | Smith et al. | | 2007/0175959 A1 | 8/2007 | Shelton, IV et al. |
| 7,407,075 B2 | 8/2008 | Holsten et al. | | 2007/0175964 A1 | 8/2007 | Shelton, IV et al. |
| 7,407,078 B2 | 8/2008 | Shelton, IV et al. | | 2007/0179476 A1 | 8/2007 | Shelton, IV et al. |
| 7,410,086 B2 | 8/2008 | Ortiz et al. | | 2007/0194079 A1 | 8/2007 | Hueil et al. |
| 7,416,101 B2 | 8/2008 | Shelton, IV et al. | | 2007/0194080 A1 | 8/2007 | Swayze et al. |
| 7,422,136 B1 | 9/2008 | Marczyk | | 2007/0194081 A1 | 8/2007 | Hueil et al. |
| 7,422,139 B2 | 9/2008 | Shelton, IV et al. | | 2007/0194082 A1 | 8/2007 | Morgan et al. |
| 7,431,188 B1 | 10/2008 | Marczyk | | 2007/0233053 A1 | 10/2007 | Shelton, IV et al. |
| 7,431,189 B2 | 10/2008 | Shelton, IV et al. | | 2007/0246505 A1 | 10/2007 | Pace-Floridia et al. |
| 7,434,717 B2 | 10/2008 | Shelton, IV et al. | | 2007/0262116 A1 | 11/2007 | Hueil et al. |
| 7,438,209 B1 | 10/2008 | Hess et al. | | 2007/0295780 A1 | 12/2007 | Shelton et al. |
| 7,441,684 B2 | 10/2008 | Shelton, IV et al. | | 2008/0029570 A1 | 2/2008 | Shelton et al. |
| 7,441,685 B1 | 10/2008 | Boudreaux | | 2008/0029573 A1 | 2/2008 | Shelton et al. |
| 7,448,525 B2 | 11/2008 | Shelton, IV et al. | | 2008/0029574 A1 | 2/2008 | Shelton et al. |
| 7,464,846 B2 | 12/2008 | Shelton, IV et al. | | 2008/0029575 A1 | 2/2008 | Shelton et al. |
| 7,464,849 B2 | 12/2008 | Shelton, IV et al. | | 2008/0029576 A1 | 2/2008 | Shelton et al. |
| 7,467,740 B2 | 12/2008 | Shelton, IV et al. | | 2008/0078800 A1 | 4/2008 | Hess et al. |
| 7,472,815 B2 | 1/2009 | Shelton, IV et al. | | 2008/0078801 A1 | 4/2008 | Shelton et al. |
| 7,490,749 B2 | 2/2009 | Schall et al. | | 2008/0078802 A1 | 4/2008 | Hess et al. |
| 7,494,039 B2 * | 2/2009 | Racenet et al. ............ 227/180.1 | | 2008/0078803 A1 | 4/2008 | Shelton et al. |
| 7,500,979 B2 | 3/2009 | Hueil et al. | | 2008/0078804 A1 | 4/2008 | Shelton et al. |
| 7,506,791 B2 | 3/2009 | Omaits et al. | | 2008/0078805 A1 | 4/2008 | Omaits et al. |
| 2003/0216778 A1 | 11/2003 | Weadock | | 2008/0078806 A1 | 4/2008 | Omaits et al. |
| 2004/0028502 A1 | 2/2004 | Cummins | | 2008/0078807 A1 | 4/2008 | Hess et al. |
| 2004/0097987 A1 | 5/2004 | Pugsley et al. | | 2008/0078808 A1 | 4/2008 | Hess et al. |
| 2004/0111081 A1 | 6/2004 | Whitman et al. | | 2008/0082115 A1 | 4/2008 | Morgan et al. |
| 2004/0122471 A1 | 6/2004 | Toby et al. | | 2008/0082124 A1 | 4/2008 | Hess et al. |
| 2004/0167572 A1 | 8/2004 | Roth et al. | | 2008/0082125 A1 | 4/2008 | Murray et al. |
| 2004/0232196 A1 | 11/2004 | Shelton, IV et al. | | 2008/0082126 A1 | 4/2008 | Murray et al. |
| 2004/0232199 A1 | 11/2004 | Shelton, IV et al. | | 2008/0164296 A1 | 7/2008 | Shelton et al. |
| 2004/0243176 A1 | 12/2004 | Hahnen et al. | | 2008/0167522 A1 | 7/2008 | Giordano et al. |
| 2005/0006434 A1 | 1/2005 | Wales et al. | | 2008/0167644 A1 | 7/2008 | Shelton et al. |
| 2005/0021026 A1 | 1/2005 | Baily | | 2008/0167670 A1 | 7/2008 | Shelton et al. |
| 2005/0070958 A1 | 3/2005 | Swayze et al. | | 2008/0167671 A1 | 7/2008 | Giordano et al. |
| 2005/0103819 A1 | 5/2005 | Racenet et al. | | 2008/0167672 A1 | 7/2008 | Giordano et al. |
| 2005/0107824 A1 | 5/2005 | Hillstead et al. | | 2008/0167736 A1 | 7/2008 | Swayze et al. |
| 2005/0131390 A1 | 6/2005 | Heinrich et al. | | 2008/0169328 A1 | 7/2008 | Shelton |
| 2005/0165415 A1 | 7/2005 | Wales | | 2008/0169329 A1 | 7/2008 | Shelton et al. |
| 2005/0173490 A1 | 8/2005 | Shelton, IV | | 2008/0169330 A1 | 7/2008 | Shelton et al. |
| 2005/0184121 A1 | 8/2005 | Heinrich | | 2008/0169331 A1 | 7/2008 | Shelton et al. |
| 2005/0187576 A1 | 8/2005 | Whitman et al. | | 2008/0169332 A1 | 7/2008 | Shelton et al. |
| 2005/0203550 A1 | 9/2005 | Laufer et al. | | 2008/0169333 A1 | 7/2008 | Shelton et al. |
| 2005/0230453 A1 | 10/2005 | Viola | | 2008/0210738 A1 | 9/2008 | Shelton et al. |
| 2005/0263562 A1 | 12/2005 | Shelton, IV et al. | | 2008/0237296 A1 | 10/2008 | Boudreaux et al. |
| 2005/0274768 A1 | 12/2005 | Cummins et al. | | 2008/0237298 A1 | 10/2008 | Schall et al. |
| 2006/0011699 A1 | 1/2006 | Olson et al. | | 2008/0296343 A1 | 12/2008 | Schall et al. |
| 2006/0025813 A1 | 2/2006 | Shelton et al. | | 2008/0296345 A1 | 12/2008 | Shelton, IV et al. |
| 2006/0025816 A1 | 2/2006 | Shelton | | 2008/0296346 A1 | 12/2008 | Shelton, IV et al. |
| 2006/0049229 A1 | 3/2006 | Milliman et al. | | 2008/0296347 A1 | 12/2008 | Shelton, IV et al. |
| 2006/0100643 A1 | 5/2006 | Laufer et al. | | 2008/0300579 A1 | 12/2008 | Broehl et al. |
| 2006/0122636 A1 | 6/2006 | Bailley et al. | | 2008/0300580 A1 | 12/2008 | Shelton, IV et al. |
| 2006/0142772 A1 | 6/2006 | Ralph et al. | | 2008/0300613 A1 | 12/2008 | Shelton, IV et al. |
| 2006/0151567 A1 | 7/2006 | Roy | | 2008/0308601 A1 | 12/2008 | Timm et al. |
| 2006/0190028 A1 | 8/2006 | Wales et al. | | 2008/0308602 A1 | 12/2008 | Timm et al. |
| 2006/0226196 A1 | 10/2006 | Hueil et al. | | 2008/0308603 A1 | 12/2008 | Shelton, IV et al. |
| 2006/0273135 A1 | 12/2006 | Beetel | | 2008/0308604 A1 | 12/2008 | Timm et al. |
| 2007/0023477 A1 | 2/2007 | Whitman et al. | | 2008/0308606 A1 | 12/2008 | Timm et al. |
| 2007/0045379 A1 | 3/2007 | Shelton, IV | | 2008/0308607 A1 | 12/2008 | Timm et al. |
| 2007/0102452 A1 | 5/2007 | Shelton, IV et al. | | 2008/0314954 A1 | 12/2008 | Boudreaux |
| 2007/0102453 A1 | 5/2007 | Morgan et al. | | 2008/0314955 A1 | 12/2008 | Boudreaux et al. |
| 2007/0102472 A1 | 5/2007 | Shelton, IV | | 2008/0314956 A1 | 12/2008 | Boudreaux |

| | | | | | | |
|---|---|---|---|---|---|---|
| 2008/0314957 | A1 | 12/2008 | Boudreaux | EP | 0503662 B1 | 6/1997 |
| 2008/0314961 | A1 | 12/2008 | Boudreaux et al. | EP | 0625335 B1 | 11/1997 |
| 2008/0314962 | A1 | 12/2008 | Boudreaux | EP | 0552423 B1 | 1/1998 |
| 2009/0001121 | A1 | 1/2009 | Hess et al. | EP | 0592244 B1 | 1/1998 |
| 2009/0001123 | A1 | 1/2009 | Morgan et al. | EP | 0648476 B1 | 1/1998 |
| 2009/0001124 | A1 | 1/2009 | Hess et al. | EP | 0676173 B1 | 9/1998 |
| 2009/0001125 | A1 | 1/2009 | Hess et al. | EP | 0603472 B1 | 11/1998 |
| 2009/0001126 | A1 | 1/2009 | Hess et al. | EP | 0605351 B1 | 11/1998 |
| 2009/0001128 | A1 | 1/2009 | Weisenburgh, II et al. | EP | 0878169 A1 | 11/1998 |
| 2009/0001130 | A1 | 1/2009 | Hess et al. | EP | 0879742 A1 | 11/1998 |
| 2009/0005807 | A1 | 1/2009 | Hess et al. | EP | 0760230 B1 | 2/1999 |
| 2009/0005808 | A1 | 1/2009 | Hess et al. | EP | 0537572 B1 | 6/1999 |
| 2009/0005809 | A1 | 1/2009 | Hess et al. | EP | 0552050 B1 | 5/2000 |
| 2009/0012556 | A1 | 1/2009 | Boudreaux et al. | EP | 1 086 713 B1 | 3/2001 |
| 2009/0076534 | A1 | 3/2009 | Shelton, IV et al. | EP | 1090592 A1 | 4/2001 |
| 2009/0200355 | A1 | 8/2009 | Baxter, III et al. | EP | 1256318 B1 | 5/2001 |
| 2009/0206123 | A1 | 8/2009 | Doll et al. | EP | 0908152 B1 | 1/2002 |
| 2009/0206124 | A1 | 8/2009 | Hall et al. | EP | 0872213 B1 | 5/2002 |
| 2009/0206125 | A1 | 8/2009 | Huitema et al. | EP | 1238634 A2 | 9/2002 |
| 2009/0206126 | A1 | 8/2009 | Huitema et al. | EP | 0656188 B1 | 1/2003 |
| 2009/0206128 | A1 | 8/2009 | Hueil et al. | EP | 0829235 B1 | 6/2003 |
| 2009/0206129 | A1 | 8/2009 | Doll et al. | EP | 0813843 B1 | 10/2003 |
| 2009/0206130 | A1 | 8/2009 | Hall et al. | EP | 0741996 B1 | 2/2004 |
| 2009/0206131 | A1 | 8/2009 | Weisenburgh, II et al. | EP | 0705570 B1 | 4/2004 |
| 2009/0206132 | A1 | 8/2009 | Hueil et al. | EP | 1426012 A1 | 6/2004 |
| 2009/0206133 | A1 | 8/2009 | Morgan et al. | EP | 0888749 B1 | 9/2004 |
| 2009/0206134 | A1 | 8/2009 | Swayze et al. | EP | 1477119 A1 | 11/2004 |
| 2009/0206135 | A1 | 8/2009 | Hall et al. | EP | 1479345 A1 | 11/2004 |
| 2009/0206136 | A1 | 8/2009 | Moore et al. | EP | 1479347 A1 | 11/2004 |
| 2009/0206137 | A1 | 8/2009 | Hall et al. | EP | 1479348 A1 | 11/2004 |
| 2009/0206138 | A1 | 8/2009 | Smith et al. | EP | 1520521 A1 | 4/2005 |
| 2009/0206139 | A1 | 8/2009 | Hall et al. | EP | 1520523 A1 | 4/2005 |
| 2009/0206140 | A1 | 8/2009 | Scheib et al. | EP | 1520525 A1 | 4/2005 |
| 2009/0206141 | A1 | 8/2009 | Huitema et al. | EP | 1522264 A1 | 4/2005 |
| 2009/0206142 | A1 | 8/2009 | Huitema et al. | EP | 1550408 A1 | 7/2005 |
| 2009/0206143 | A1 | 8/2009 | Huitema et al. | EP | 1557129 A1 | 7/2005 |
| 2009/0206144 | A1 | 8/2009 | Doll et al. | EP | 1064883 B1 | 8/2005 |
| 2009/0209946 | A1 | 8/2009 | Swayze et al. | EP | 1157666 81 | 9/2005 |
| | | | | EP | 1621138 A2 | 2/2006 |
| | | FOREIGN PATENT DOCUMENTS | | EP | 1621141 A2 | 2/2006 |
| | | | | EP | 1621145 A2 | 2/2006 |
| CA | | 2512960 A1 | 1/2006 | EP | 1652481 A2 | 5/2006 |
| CA | | 2514274 A1 | 1/2006 | EP | 1382303 B1 | 6/2006 |
| DE | | 273689 C | 5/1914 | EP | 1045672 B1 | 8/2006 |
| DE | | 1775926 A | 1/1972 | EP | 1617768 B1 | 8/2006 |
| DE | | 9412228 U | 9/1994 | EP | 1702567 A2 | 9/2006 |
| DE | | 19924311 A1 | 11/2000 | EP | 1129665 B1 | 11/2006 |
| DE | | 69328576 T2 | 1/2001 | EP | 1256317 B1 | 12/2006 |
| DE | | 20112837 U1 | 10/2001 | EP | 1728473 A1 | 12/2006 |
| DE | | 20121753 U1 | 4/2003 | EP | 1728475 A2 | 12/2006 |
| DE | | 10314072 A1 | 10/2004 | EP | 1479346 B1 | 1/2007 |
| EP | | 0122046 A1 | 10/1984 | EP | 1484024 B1 | 1/2007 |
| EP | | 0033548 B1 | 5/1986 | EP | 1754445 A2 | 2/2007 |
| EP | | 0276104 A2 | 7/1988 | EP | 1759812 A1 | 3/2007 |
| EP | | 0639349 A2 | 2/1994 | EP | 1785097 A2 | 5/2007 |
| EP | | 0593920 A1 | 4/1994 | EP | 1790293 A2 | 5/2007 |
| EP | | 0600182 A2 | 6/1994 | EP | 1300117 B1 | 8/2007 |
| EP | | 0630612 A1 | 12/1994 | EP | 1813199 A1 | 8/2007 |
| EP | | 0634144 A1 | 1/1995 | EP | 1813207 A1 | 8/2007 |
| EP | | 0646356 A2 | 4/1995 | EP | 1872727 A1 | 1/2008 |
| EP | | 0646357 A1 | 4/1995 | EP | 1839596 A2 | 2/2008 |
| EP | | 0653189 A2 | 5/1995 | EP | 1897502 A1 | 3/2008 |
| EP | | 0669104 A1 | 8/1995 | EP | 1749486 B1 | 3/2009 |
| EP | | 0679367 A2 | 11/1995 | FR | 999646 A | 2/1952 |
| EP | | 0392547 B1 | 12/1995 | FR | 1112936 A | 3/1956 |
| EP | | 0685204 A1 | 12/1995 | FR | 2765794 A | 1/1999 |
| EP | | 0699418 A1 | 3/1996 | GB | 939929 A | 10/1963 |
| EP | | 0702937 A1 | 3/1996 | GB | 1210522 A | 10/1970 |
| EP | | 0705571 A1 | 4/1996 | GB | 2336214 A | 10/1999 |
| EP | | 0484677 B2 | 6/1996 | JP | 6007357 A | 1/1994 |
| EP | | 0541987 B1 | 7/1996 | JP | 7051273 A | 2/1995 |
| EP | | 0667119 B1 | 7/1996 | JP | 8033641 A | 2/1996 |
| EP | | 0770355 A1 | 5/1997 | JP | 8229050 A | 9/1996 |

| | | | |
|---|---|---|---|
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/35464 A1 | 11/1996 |
| WO | WO 97/34533 A1 | 9/1997 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/043571 A2 | 6/2002 |
| WO | WO 02/058568 A1 | 8/2002 |
| WO | WO 02/067785 A2 | 9/2002 |
| WO | WO 02/098302 A1 | 12/2002 |
| WO | WO 03/000138 A1 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/132992 A1 | 12/2006 |
| WO | WO 2007/016290 A2 | 2/2007 |
| WO | WO 2007/121579 A1 | 11/2007 |
| WO | WO 2007/142625 A2 | 12/2007 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

U.S. Nonprovisional Patent Application for Surgical Stapling Instrument Having an Electroactive Polymer Actuated Medical Substance Dispenser, Inventors: Frederick E. Shelton IV, Joseph C. Hueil, Jerry R. Morgan.

European Search Report, Application No. 06255734.3, dated Jun. 22, 2009 (10 pages).

* cited by examiner

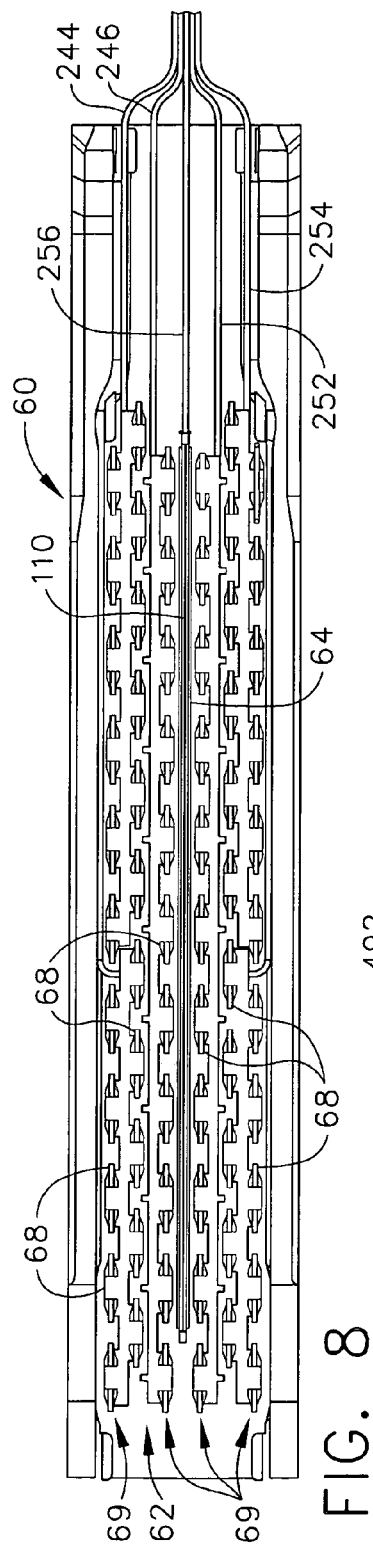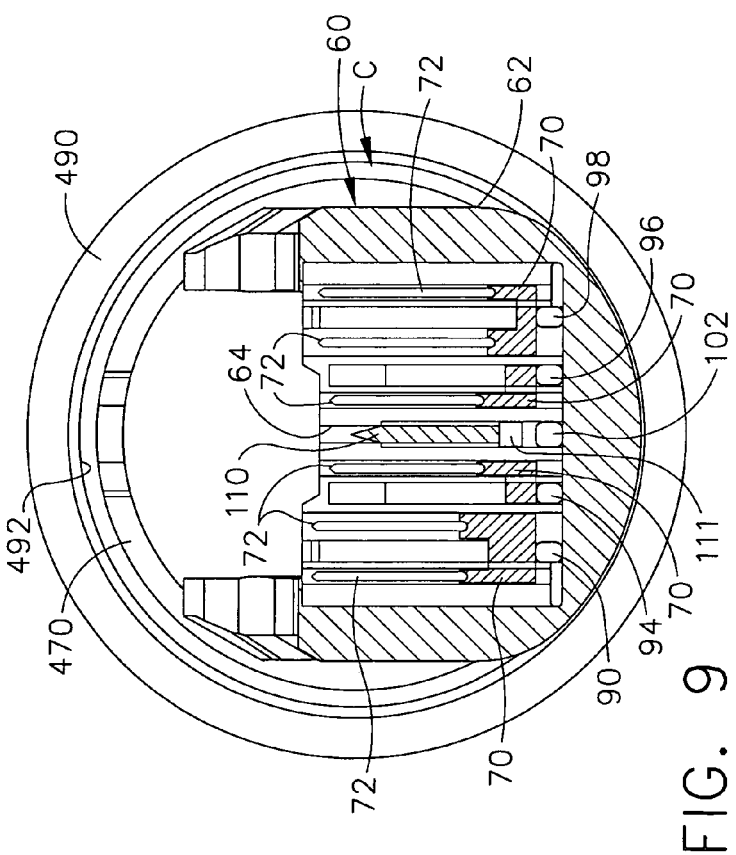

ARTICULATION JOINT WITH IMPROVED MOMENT ARM EXTENSION FOR ARTICULATING AN END EFFECTOR OF A SURGICAL INSTRUMENT

FIELD OF THE INVENTION

The present invention relates in general to surgical instruments that are suitable for endoscopically inserting an end effector (e.g., endocutter, grasper, cutter, staplers clip applier, access device, drug/gene therapy delivery device, an energy device using ultrasound, RF, laser, etc.) and, more particularly, to endocutters with articulating end effectors.

BACKGROUND OF THE INVENTION

Endoscopic surgical instruments are often preferred over traditional open surgical devices since a smaller incision tends to reduce the post-operative recovery time and complications. Generally, these endoscopic surgical instruments include an "end effector", a handle assembly and a long shaft that extends between the end effector and the handle assembly. The end effector is the portion of the instrument configured to engage the tissue in various ways to achieve a desired diagnostic or therapeutic effect (e.g., endocutter, grasper, cutter, staplers, clip applier, access device, drug/gene therapy delivery device, and energy device using ultrasound, RF, laser, etc.). The end effector and the shaft portion are sized to be inserted through a trocar placed into the patient. The elongated shaft portion enables the end effector to be inserted to a desired depth and also facilitates some rotation of the end effector to position it within the patient. With judicious placement of the trocar and use of graspers, for instance, through another trocar, often this amount of positioning is sufficient. Surgical stapling and severing instruments, such as those described in U.S. Pat. No. 5,465,895, are an example of an endoscopic surgical instrument that successfully positions an end effector by insertion and rotation.

Depending upon the nature of the operation, it may be desirable to further adjust the positioning of the end effector of an endoscopic surgical instrument. In particular, it is often desirable to orient the end effector at an angle relative to the longitudinal axis of the shaft of the instrument. The transverse or non-axial movement of the end effector relative to the instrument shaft is often conventionally referred to as "articulation". This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation. Still other examples of articulatable surgical stapling devices are disclosed in U.S. Pat. Nos. 6,250,532 and 6,644,532.

Due to the types end effector firing systems commonly employed, the actuator arrangements for articulating the end effector must often generate high amounts of torque to bend the firing structure. This problem is exacerbated by the lack of available space for accommodating actuating devices that are large enough to generated those required forces.

Consequently, a significant need exists for an articulating surgical instrument that incorporates an articulation mechanism that can generate the torque necessary to selectively articulate the end effector thereof in a desired manner.

BRIEF SUMMARY OF THE INVENTION

In accordance with one embodiment of the present invention there is provided a surgical instrument that comprises a handle assembly and an elongated tube assembly coupled to the handle assembly. In one non-limiting embodiment, the elongated tube assembly comprises a proximal tube segment that has a proximal tube wall and that is attached to the handle assembly. The tube assembly further comprises a distal tube segment that is pivotally attached to the proximal tube segment such that it is selectively pivotable between a position wherein the distal tube segment is substantially in axial alignment with the proximal tube segment and positions wherein the distal tube segment is not substantially axially aligned with the proximal tube segment. The distal tube segment also has a distal wall. An actuator assembly is supported by at least one of the proximal and distal tube segments and is coupled to at least one portion of one of the proximal and distal walls such that, upon actuation of the actuator assembly, the portion of one of the proximal and distal walls is pivoted out of alignment with a corresponding portion of one of the proximal and distal walls to cause the distal tube segment to articulate out of substantial axial alignment with the proximal tube segment. A surgical implement is attached to the distal tube segment.

In accordance with another non-limiting embodiment of the present invention there is provided a surgical instrument that comprises a handle assembly and an elongated tube assembly that is coupled to the handle assembly. In one non-limiting embodiment, the elongated tube assembly comprises a proximal tube segment that is attached to the handle assembly and a distal tube segment that is pivotally coupled to the proximal tube segment by a pivot pin. An actuator is supported by one of the proximal and distal tube segments and has an extendable and retractable actuation rod. A moment arm rod is coupled to the actuation rod and slidably extends through an opening in the pivot pin such that by extending and retracting the actuation rod, the distal tube segment is pivoted about the pivot pin relative to the proximal tube segment. A surgical implement is attached to the distal tube segment.

In accordance with another embodiment of the present invention there is provided a method of performing a surgical procedure through a trocar installed in a patient. One form of the method comprises providing a surgical instrument that has a handle assembly and a manipulatable surgical implement articulatably attached to the handle assembly by a tube assembly. The tube assembly includes a proximal tube segment that is attached to the handle assembly. The proximal tube segment is sized to permit the proximal tube segment to axially pass through the trocar. The tube assembly further comprises a distal tube segment that is attached to the surgical implement and is pivotally coupled to the proximal tube segment for selective pivotal travel about a pivot axis. The distal tube segment is sized to permit the distal tube segment to axially pass through the trocar. An actuator is supported by one of the proximal and distal tube segments. The actuator has a selectively extendable and retractable actuation rod wherein a portion of the actuation rod is attached to the other of the proximal and distal tube segments at a point of attachment to define a moment arm between the pivot axis and the point of attachment. The method further comprises substantially coaxially aligning the proximal and distal tube segments and passing the surgical implement and the coaxially aligned distal and proximal tube segments through the trocar into the patient. The method also comprises increasing a length of the moment arm to pivot the distal tube segment and surgical implement out of coaxial alignment with the proximal tube segment.

One feature of various embodiments of the present invention is to provide an articulation joint that enables the proximal and distal tube segments to be substantially coaxially aligned for insertion through a passageway in a trocar and then articulated relative to each other after the joint has passed through the trocar. Various embodiments of the articulation joint provide a means for increasing the length of the moment arm between the actuator and the pivot point between the proximal and distal tube segments such that improved articulation forces may be achieved. Accordingly, various embodiments of the invention provide solutions to the shortcomings of other articulated surgical instruments that are designed to be passed through a trocar or similar structure. Those of ordinary skill in the art will readily appreciate, however, that these and other details, features and advantages will become further apparent as the following detailed description proceeds.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain various principles of the various embodiments of the present invention.

FIG. 8 is a plan view of a staple cartridge installed in an end effector depicted in FIGS. 6 and 7;

FIG. 9 is a cross-sectional end view illustrating the end effector inserted into a trocar passageway;

DETAILED DESCRIPTION OF THE INVENTION

Figure 1:
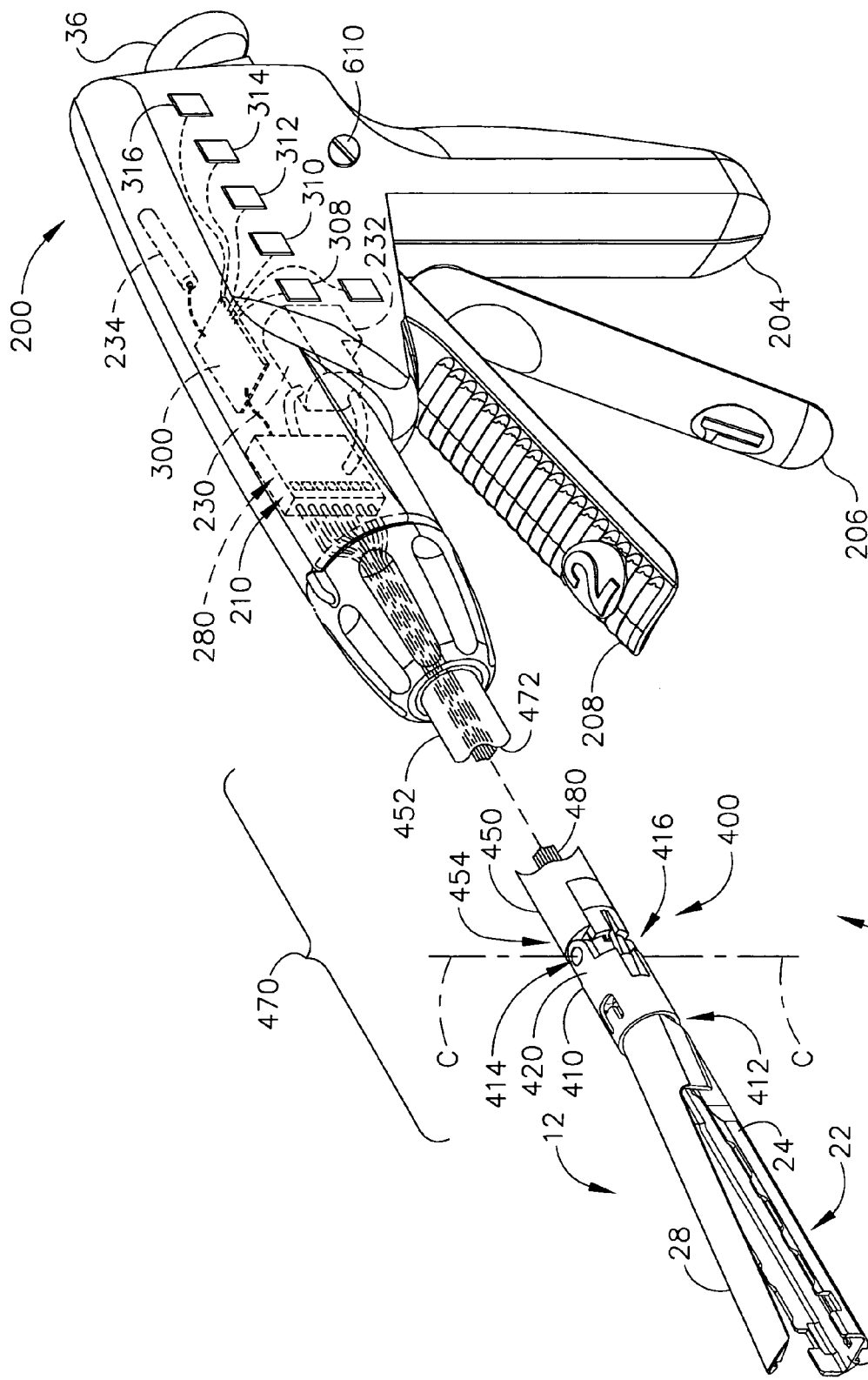
FIG. 1 is a partial perspective view of one non-limiting embodiment of a moment arm extension arrangement employed in connection with a hydraulically operated endocutter with the tube segments thereof in a first substantially coaxially aligned position.
Figure 2:
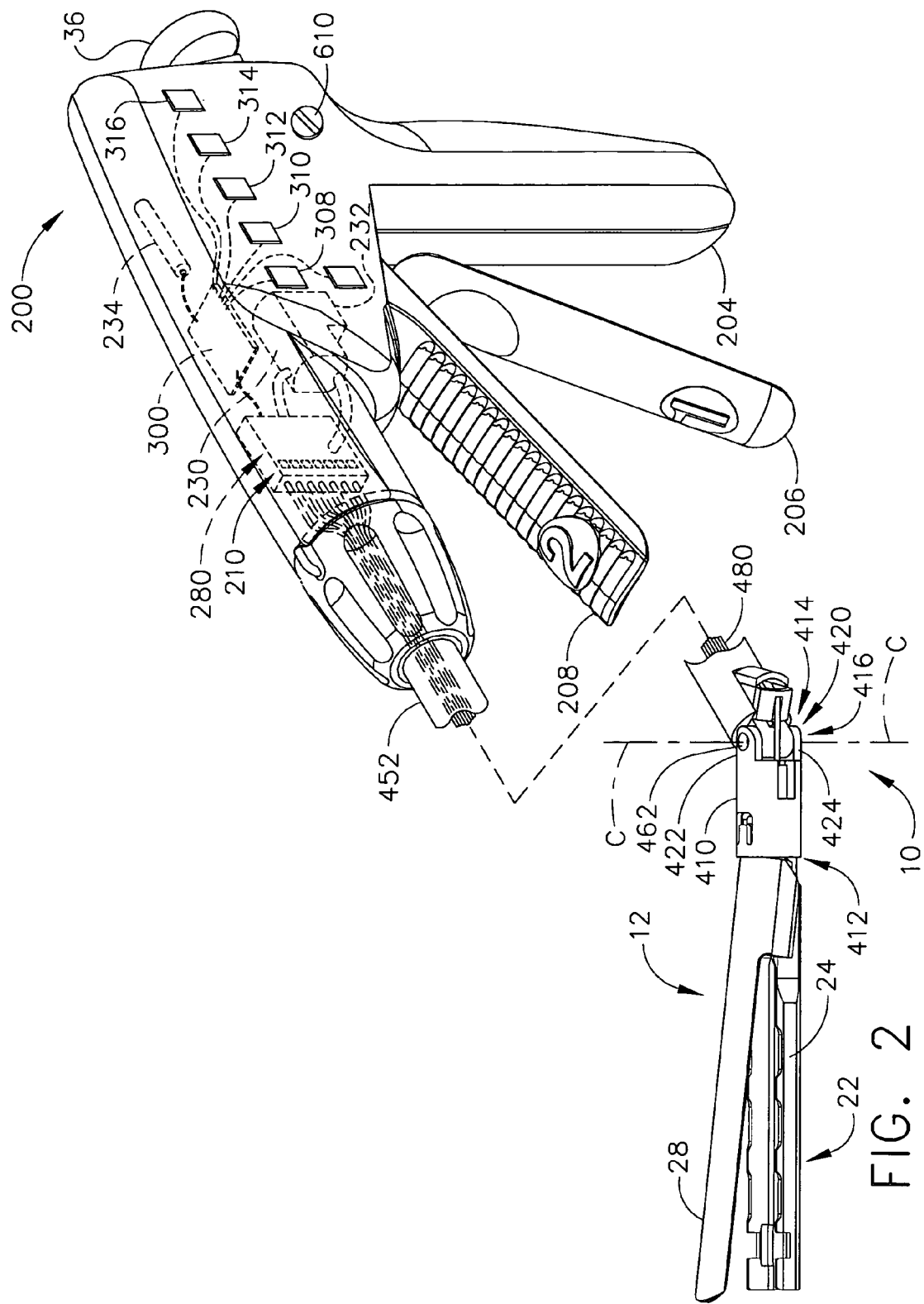
FIG. 2 is another perspective view of the moment arm extension arrangement and endocutter of FIG. 1 with the tube segments articulated at an angle relative to each other.

Turning to the Figures, wherein like numerals denote like components throughout the several views, FIGS. 1 and 2 depict one embodiment of a surgical instrument 10 that is capable of practicing the unique benefits of the present invention. As can be seen in FIGS. 1 and 2, the instrument 10 includes a handle assembly 200 and a surgical implement portion 12. As used herein, the term "surgical implement" refers to a component or set of components configured to engage tissue to accomplish a surgical task. Examples of surgical implements include, but are not limited to: endocutters, graspers, clamps, cutters, staplers, clip appliers, probes or access devices, drug/gene therapy delivery devices, energy devices such as ultrasound, RF, or laser devices, etc.

In the non-limiting embodiment depicted in the Figures, the surgical instrument 10 includes a hydraulically actuated end effector 22 and handle arrangement 200 of the type disclosed in the U.S. patent application Ser. No. 11/270,217, entitled "SURGICAL INSTRUMENT HAVING A HYDRAULICALLY ACTUATED END EFFECTOR" to Frederick E. Shelton IV and Jerome R. Morgan, that was filed on even date herewith and which is commonly owned with the present application and which the disclosure thereof is hereby incorporated by reference in its entirety. As the present Detailed Description proceeds, however, the skilled artisan will readily appreciate that the unique and novel features of the various embodiments of the present invention may also be employed in connection with electrically actuated or pneumatically actuated end effectors. Thus, the various embodiments of the present invention may be advantageously employed in connection with a variety of surgical implements other than the exemplary embodiment depicted in the Figures without departing from the spirit and scope of the present invention. Accordingly, the scope of protection afforded to the various embodiments of the present invention should not be limited to use only with the specific type of surgical implements specifically described herein.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 3:
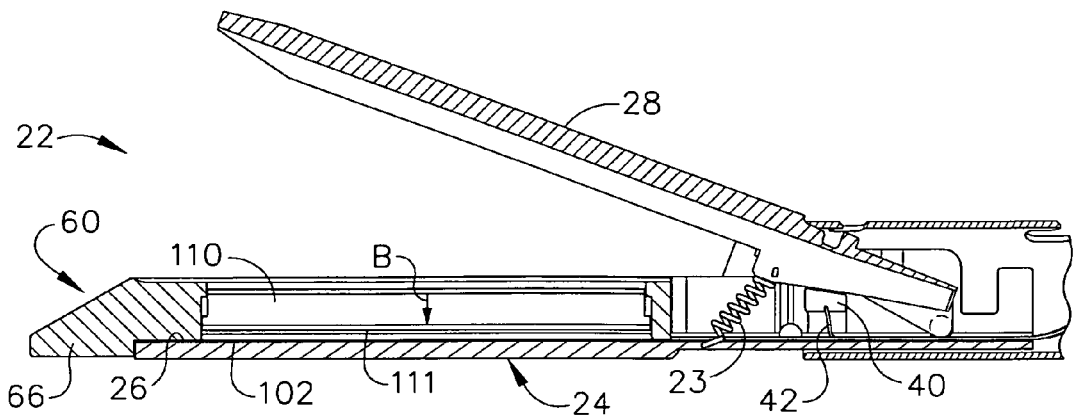
FIG. 3 is a partial cross-sectional view of an end effector employed in the endocutter depicted in FIGS. 1 and 2 with the anvil thereof in an open or unclamped position with some of the elements thereof omitted for clarity.
Figure 4:
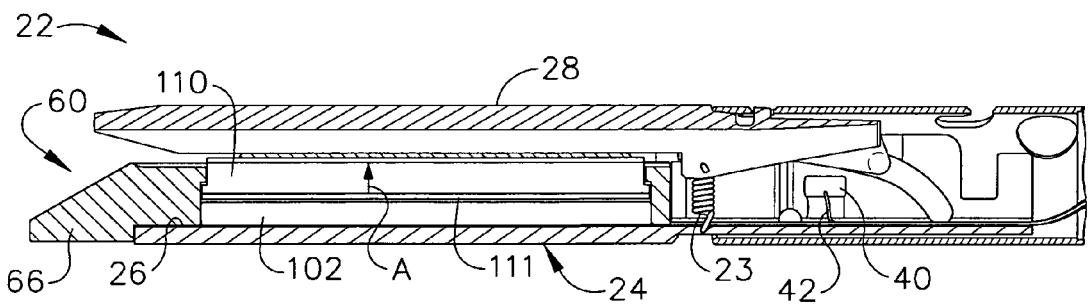
FIG. 4 is another cross-sectional view of the end effector of FIG. 3 in a closed or clamped position with the cutting bar in an extended position.
Figure 5:
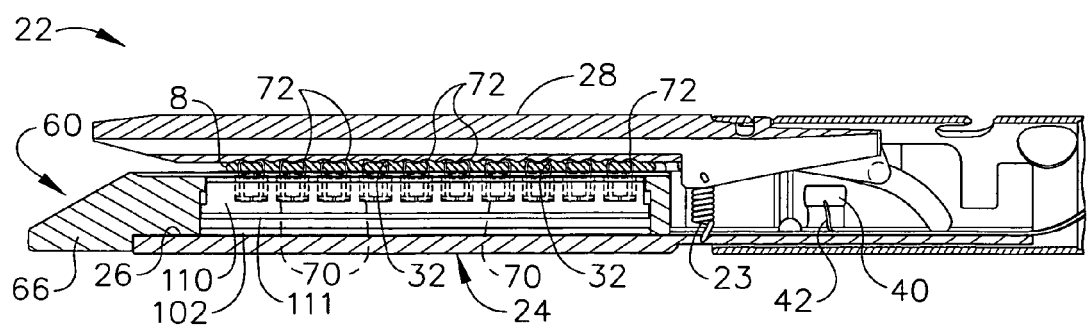
FIG. 5 is another cross-sectional view of the end effector of FIGS. 3 and 4 showing tissue after being cut and stapled therein.
Figure 10:
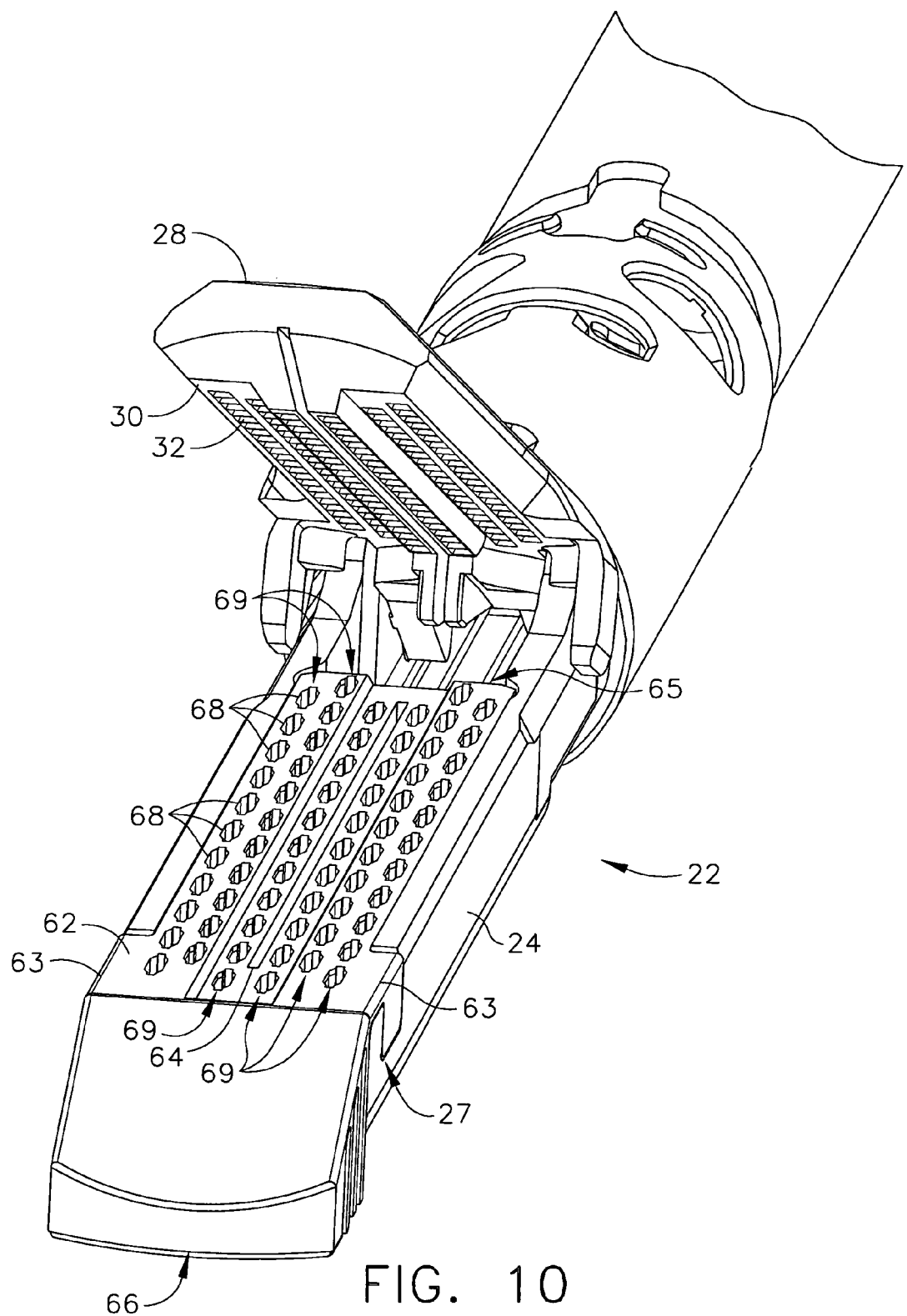
FIG. 10 is a perspective view of a cartridge installed in an end effector with the anvil thereof in an open or unclamped position.

FIGS. 3-10 show views of one type of end effector 22 configured to perform clamping, severing and stapling of tissue according to various embodiments the present invention. In one embodiment, the end effector 22 has a body portion 24 that is provided with an elongate channel 26 for receiving a staple cartridge 60 therein. An anvil 28 is coupled to the body portion 24 and is capable of being selectively pivoted toward and away from cartridge 60 mounted in the elongate channel 26. FIGS. 3 and 10 illustrate the anvil 28 in an open position and FIGS. 4 and 5 illustrate the anvil 28 in a closed position. The anvil 28 may be closed hydraulically and returned to its open position by an energy storing device such as a spring 23. As can be seen in FIGS. 3-5, an actuation bladder 40 may be strategically mounted below a portion of the anvil 28 such that when the bladder 40 is inflated with a pressurized fluid or air, it biases the anvil 28 to its open position. A supply line 42 is coupled to the bladder 40 for supplying pressurized fluid from a reservoir 232 as will be described in further detail below. In alternative non-limiting embodiments, an additional hydraulic cylinder or cylinder(s) may be advantageously employed to open and close the anvil. Still in other non-limiting embodiments, the anvil 28 may be opened and closed by slidable action of a distal tube segment 410 attached thereto.

One type of cartridge that may be used with such end effector is also depicted in FIGS. 3-10. The staple cartridge 60 has a cartridge body 62 that is divided by an elongated cutting slot 64 that extends from a proximal end 65 of the cartridge 60 toward a tapered outer tip 66. See FIG. 10. A plurality of staple-receiving channels 68 are formed within the staple cartridge body 64 and are arranged in spaced longitudinal rows 69 on each side of the elongated cutting slot 64. Positioned within the staple-receiving channels are staple drivers 70 that each support one or more staples 72 thereon. The staples 72 are advanced or "fired" by moving their respective drivers 70 in an upward direction toward the anvil 28.

FIG. 10 depicts a three dimensional view of the end effector 22 in an open position with a staple cartridge 60 installed in the elongate channel 26. On a lower surface 30 of the anvil 28, a plurality of staple-forming pockets 32 are arrayed to correspond to each staple receiving channel 68 in the cartridge body 62 when the cartridge 60 is installed in the end effector 22. More specifically, each forming pocket 32 in the anvil 28 may correspond to an individual staple 72 located within the staple cartridge 60. The staple cartridge 60 may be snap-fit into the elongate channel 26. For example, extension features 63 of the staple cartridge 60 engage recesses 27 (shown in FIG. 6) of the elongate channel 26.

Figure 6:
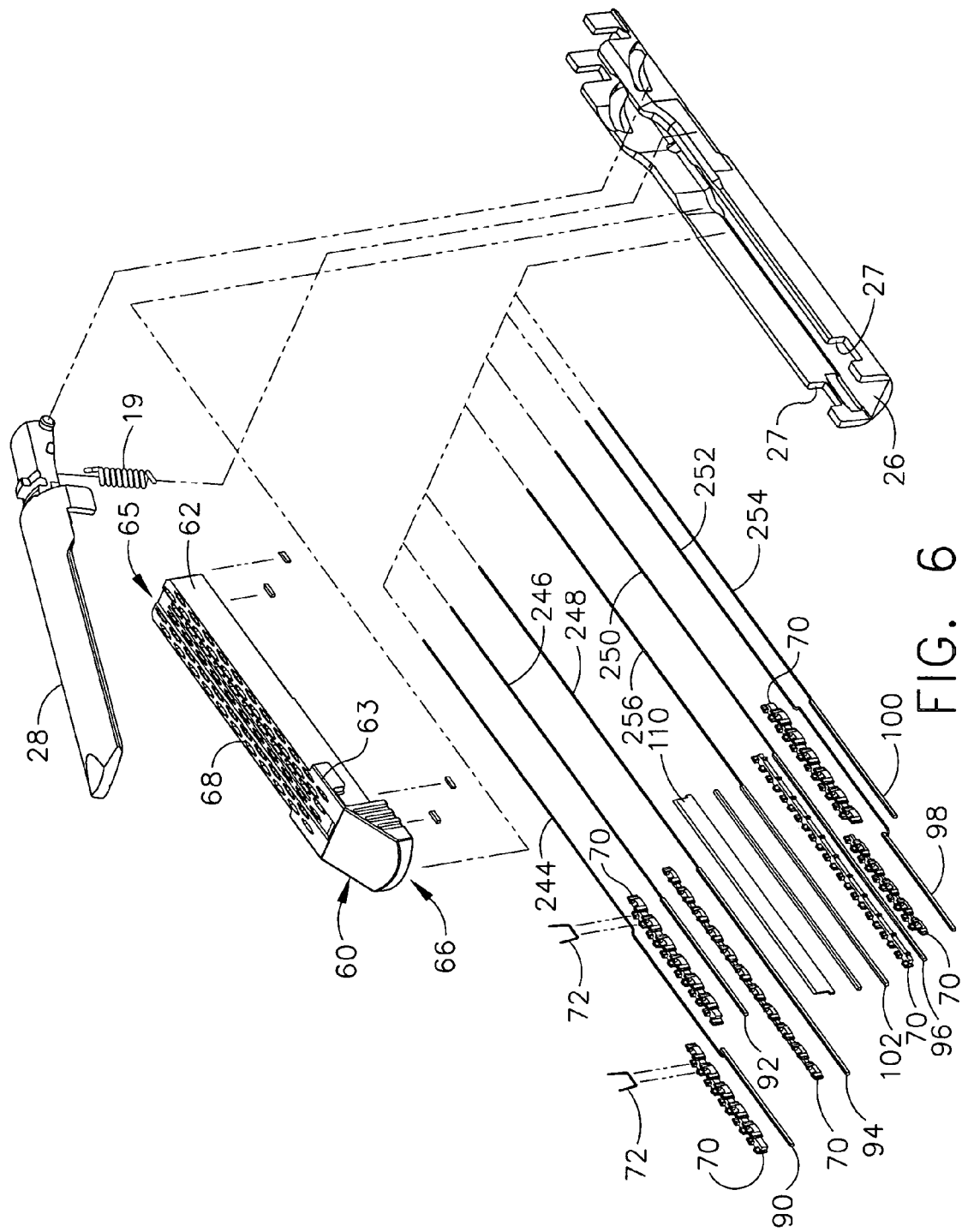
FIG. 6 is an exploded perspective view of the end effector depicted in FIGS. 1-5.
Figure 7:
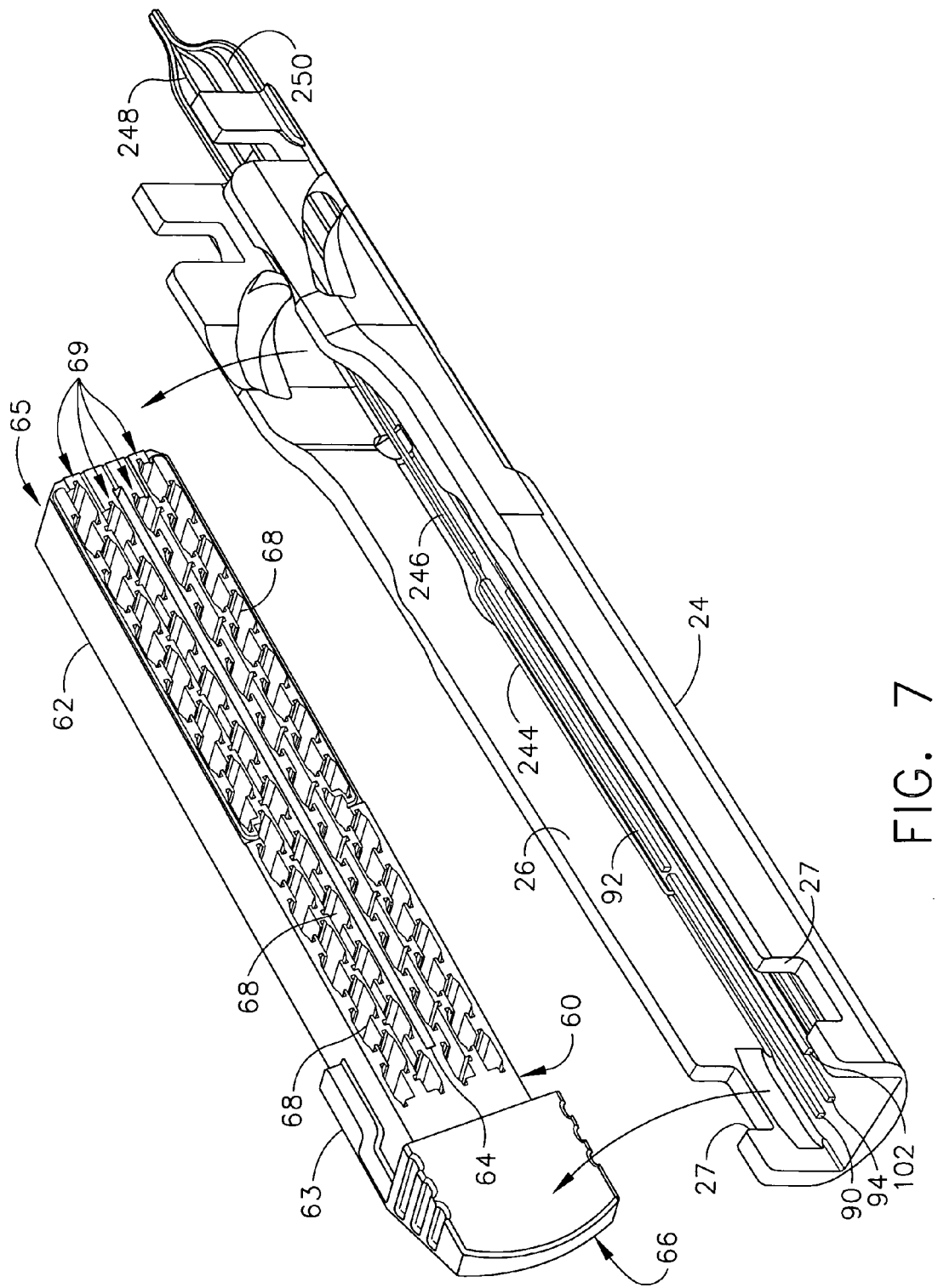
FIG. 7 is another exploded assembly view of the end effector and a staple cartridge.
Figure 11:
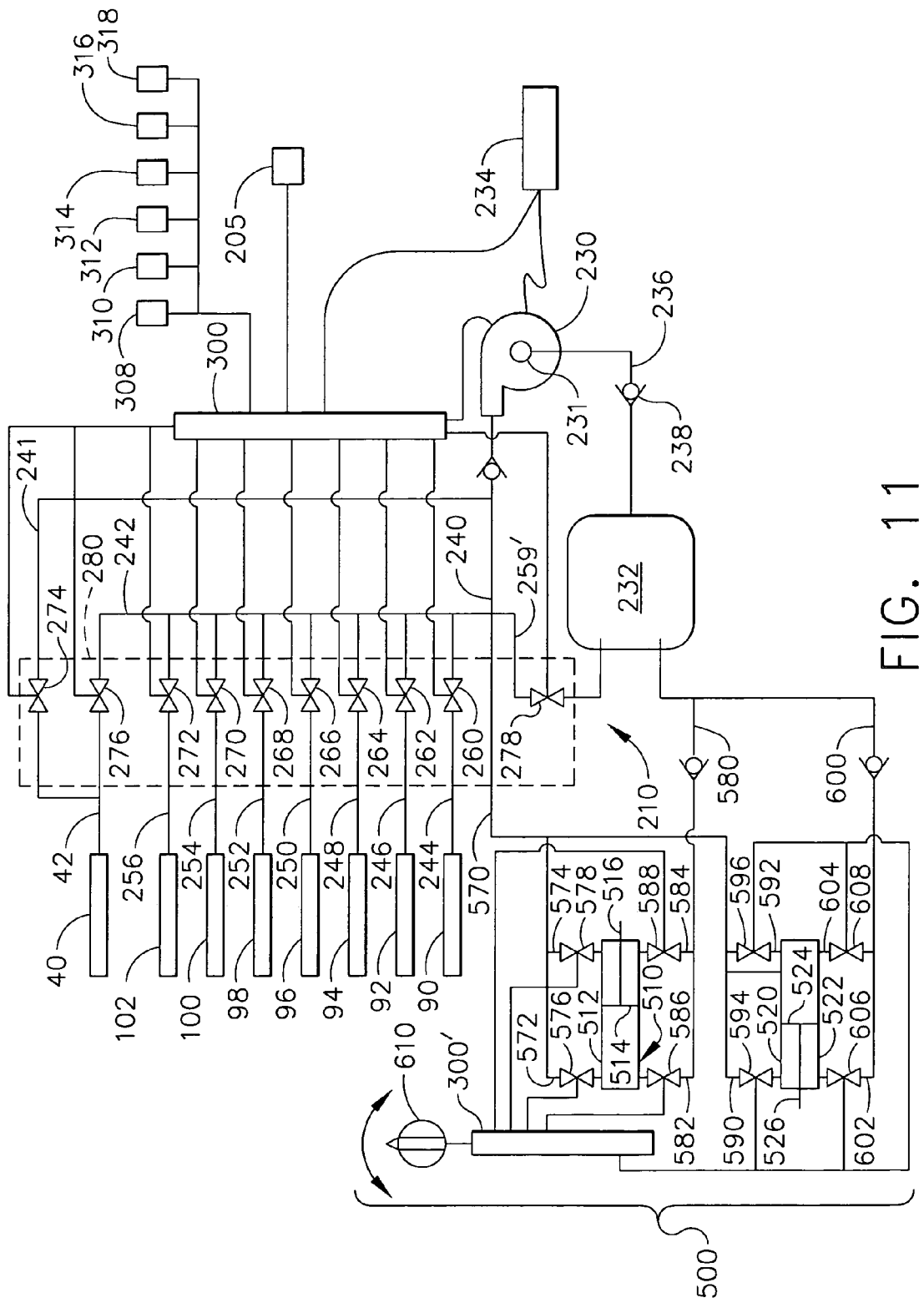
FIG. 11 is a schematic depiction of one hydraulic system embodiment of the present invention.

In one embodiment, the staple drivers 70 are driven in an "upward" (toward the anvil 28) direction by a series of hydraulically actuated bladders 90, 92, 94, 96, 98, 100 situated within the elongated slot 26 of the end effector 22 and arranged such that when the bladders 90, 92, 94, 96, 98, 100 are inflated, they drive or "fire" the corresponding drivers 70 and their respective staples 72 toward the anvil 28. As the ends of the staple legs contact the corresponding staple-forming pockets 32 in the anvil 28, they are bent over to close the staple 72. Various firing arrangements are disclosed in the above-mentioned patent application entitled "SURGICAL INSTRUMENT HAVING A HYDRAULICALLY ACTUATED END EFFECTOR" which has been herein incorporated by reference. Pressurized fluid or air is supplied to the bladders 90, 92, 94, 96, 98, 100 through a series of supply lines as shown in FIGS. 6 and 11.

Also in one embodiment, to facilitate cutting of tissue 8 clamped in the end effector 22, a hydraulically actuated cutting bar 110 is operatively mounted within the elongated channel 26 and arranged to be received within the elongated slot 64 in the cartridge body 62 when the cartridge 60 is mounted within the end effector 22. The cutting bar 110 extends longitudinally along the elongate slot 64 and is mechanically coupled to or otherwise supported on a support bar 111 which is attached to a hydraulic cutting bladder 102. By introducing a pressurized fluid or air into the cutting bladder 102, the cutting bar 110 is forced upward (represented by arrow A in FIG. 4) thereby causing the cutting bar 110 to sever the tissue 8 that is clamped between the anvil 28 and the cartridge 60. After the cutting bar 110 has severed the tissue 8, the pressurized fluid is permitted to exit the cutting bladder 102 to thereby permit the bladder 102 to deflate and permit the cutting bar 110 to move downward (arrow "B" in FIG. 3) to its retracted or unfired position. Pressurized fluid or air is supplied to the cutting bladder 102 by supply line 256.

As can be seen in FIGS. 1 and 2, the handle assembly 200 may house a hydraulic system generally designated as 210 for controlling the operation of the end effector 22. One embodiment of a hydraulic system 210 that may be employed to control the end effector 22 is depicted in schematic form in FIG. 11. In this non-limiting embodiment, a conventional hydraulic pump assembly 230 that includes a fluid reservoir 232 is employed to supply pressurized fluid to the various bladders. In one embodiment, the pump 230 is powered by a battery 234 supported within the handle assembly 200. However, the pump 230 could also be powered by other means, such as by alternating current or by a mechanical actuator. The pump 230 may be fluidically coupled to the reservoir 232 by supply line 236 that may have a conventional check valve 238 therein. See FIG. 11. As used herein, the term "fluidically coupled" means that the elements are coupled together with an appropriate supply, return, discharge, etc. line or other means to permit the passage of pressurized fluid medium, air, etc. therebetween. As used herein, the term "line" as used in "supply line", "discharge line" or "return line" refers to an appropriate fluid passage formed from conduit, pipe, tubing, etc. for transporting pressurized fluid, air, etc. from one component to another.

In one embodiment, a discharge line 240 attached to the discharge port 231 of the pump 230 is piped to a manifold 242 that has designated supply lines for each bladder coupled thereto. For example, in the embodiment depicted in FIG. 11, a supply line 244 is coupled to bladder 90 and has a control valve 260 therein for controlling the flow of pressurized fluid through the line 244 to bladder 90. Supply line 246 is coupled to bladder 92 and has a control valve 262 therein. Supply line 248 is coupled to bladder 94 and has a control valve 264 therein. Supply line 250 is coupled to bladder 96 and has a control valve 266 therein. Supply line 252 is coupled to bladder 98 and has a control valve 268 therein. Supply line 254 is coupled to bladder 100 and has a control valve 270 therein. Supply line 256 is coupled to cutting bladder 102 and has control valve 272 therein. Supply line 42 is coupled to the anvil bladder 40 and the supply line 240 by line 241. A supply valve 274 is provided in line 241 for controlling the flow of pressurized fluid thereto and a return valve 276 is provided to permit the fluid to return from the bladder 40 into the manifold line 242 and through a return line 259' that is attached to the manifold 242 and the reservoir 232. As can be seen in FIG. 11, the return line 259' may have a return valve 278 therein. Valves 262, 264, 266, 268, 270, 272, 274, 276, 278 comprise a valve unit, generally designated as 280. In various non-limiting embodiments, the valves 262, 264, 266, 268, 270, 272, 274, 276, 278 may each comprise electrically actuated valves, such as, for example, piezo valves or Electro Active Polymer (EAP) valves which may be configured in response to an electrical signal. However, other suitable valve and valve arrangements could be employed.

The above-described valves may be operated by a control circuit 300 in response to input received from input buttons, such as buttons 308, 310, 312, 314, and/or 316 located on handle. The control circuit may also be powered by the battery 234 and comprise a suitable circuit capable of generating signals for configuring valve unit 280 in response to input from buttons 308, 310, 312, 314, 316 and/or from other portions of the handle such as a closure trigger 206 and/or a firing trigger 208 that are pivotally coupled thereto. In one non-limiting embodiment, the control circuit 300 may include a microprocessor and other related components including Random Access Memory (RAM), Read Only Memory (ROM), etc. In other non-limiting embodiments, the control circuit 300 may include various logical circuit elements.

As can be seen in FIGS. 1 and 2, in one non-limiting embodiment, the handle assembly 200 of the instrument 10 includes a pistol grip 204 that includes a closure trigger 206 that is pivotally attached thereto to commence closure of the anvil 28. In one embodiment, a closure trigger sensor 205 is employed to sense when the closure trigger 206 has been pivoted to the closed position. The closure trigger sensor 205 communicates with the control circuit to open the return valve 276 and return valve 278 and close supply valve 274 to permit the pressurized fluid to return from the anvil bladder 28 into the reservoir 232. The anvil 28 is then pivoted to the closed position by the return spring 23. The closure trigger 206 may be retained in the closed position by a release button latch arrangement 36 of the type disclosed U.S. Pat. No. 6,905,057 to Jeffery S. Swayze and Frederick E. Shelton, IV entitled SURGICAL STAPLING INSTRUMENT INCORPORATING A FIRING MECHANISM HAVING A LINKED RACK TRANSMISSION, the disclosure of which is herein incorporated by reference in its entirety. Another non-limiting embodiment links the closure trigger 206 to the tube assembly 452 and causes it to move distally driving distal tube 410 over the end effector assembly 24 closing the system.

When the end effector 22 is in the closed position, it may be inserted through the trocar 490. See FIG. 9. To reopen the end effector 22, the release button 36 is pressed to unlatch the closure trigger 206 to enable it to pivot away from the firing trigger 208 to an open position. When in the open position, the closure trigger sensor 205 signals the control circuit 300 to power pump 230 and open supply valve 274 and close return valve 276. Pressurized fluid is then pumped into the anvil bladder 40 to pivot the anvil 28 to the open position. When the clinician has oriented the end effector 22 such that the desired tissue is located between the open anvil 28 and the cartridge 60, the closure trigger 206 is pivoted to the closed position and latched. Valves 276 and 278 are opened and valve 241 is closed. Valves 276 and 278 are opened for a sufficient time t0 permit the fluid in the anvil bladder 40 to be returned therefrom through the lines 42, 242 and 259. Thereafter, those valves are closed. As indicated above, the use of the hydraulically powered bladder and return spring arrangement described herein is just one type of structure that may be employed to open and close the anvil 28. Other anvil control arrangements may be employed without departing from the spirit and scope of the present invention and, therefore, the protection afforded to the various embodiments of the present invention should not be limited solely to such bladder and return spring arrangement.

Input buttons 308, 310, 312, 314, 316 may provide input signals to the control circuit 300 in any suitable way. In one non-limiting embodiment, each input button 308, 310, 312, 314, 316 may correspond to a particular valve or valves for controlling the inflation of one or more bladders. While five actuation buttons are shown for this non-limiting embodiment, the reader will appreciate that other numbers of buttons may be employed. For example, if it is desirable to only actuate one stapling bladder at a time, a separate actuation button for each bladder may be provided. For example, button 308 may control valve 272 in the cutter supply line 256. By actuating that valve 272, pressurized fluid supplied by the pump 230 into the manifold 242 is permitted to flow through the supply line 256 into the cutting bladder 102. Likewise, if actuator button 310 is used to control valves 260, 262, activating the button 310 will cause the stapling bladders 90 and 92 to inflate and fire their corresponding staples 72. Multiple buttons may be selected to create firing patterns including more than one implement. In other non-limiting embodiments, each input button 308, 310, 312, 314, 316 may represent a pre-determined firing order and/or pattern. For example, selecting a button 308, 310, 312, 314, 316 may cause the control circuit 318 to configure the valve unit 304 such that hydraulic devices corresponding to particular surgical implements are fired when the firing trigger 28 is depressed. It will be appreciated that various embodiments may have more or fewer input buttons than are shown. In one embodiment, a firing trigger 208 is pivotally attached to the handle 200 outboard of the closure trigger 206 and one or more firing sensors (not shown) may be positioned to detect the position of the firing trigger. The firing sensors would then communicate with the control circuit 300 to control the various valves to permit pressurized fluid to flow to the various staple bladders to achieve a desired firing sequence.

In various non-limiting embodiments, the valve unit 280 may be configured to introduce a delay to the driving of one or more surgical implements included in the end effector 12. For example, it may be desirable to drive a cutting implement and then delay for a predetermined time before driving one or more zones of a stapling implement. The delay may be accomplished according to any suitable method. In one non-limiting embodiment, the control circuit 300 may configure the valve unit 280 to open a path for hydraulic fluid between the hydraulic pump 230 and a first surgical implement included in the end effector 12. When the firing trigger 28 is actuated, the pump 302 may generate pressurized hydraulic fluid, which drives the first surgical implement. The control circuit 300 may sense when the first surgical implement is driven (e.g., by sensing the position of the firing trigger 208) and begin a timer that counts off a predetermined delay time. At the expiration of the predetermined delay time, the control circuit 318 may configure the valve unit 280 to provide the pressurized hydraulic fluid to a second surgical implement. Hydraulic pressure generated at the actuation of the firing trigger 208 may be sufficient to drive the second surgical implement, or in various embodiments, the hydraulic pump 230 may be utilized to generate additional hydraulic pressure.

As can be seen in FIGS. 1, 2, 12 and 13, the end effector 22 may be attached to the handle assembly 200 by an articulating joint assembly, generally designated as 400. In one non-limiting embodiment, the articulating joint assembly 400 includes a distal tube segment 410 that has a distal end 412, a proximal end 414, and a distal axis H-H (shown in FIG. 13). The distal end 412 is mechanically (e.g., rigidly or slidably connected-depending upon the anvil closure arrangement used) coupled to the end effector body 24. The joint assembly 400 further includes a proximal tube segment 450 that has a proximal end 452, a distal end 454, and a proximal axis I-I. The proximal end 452 is mechanically attached to the handle assembly 200. In one embodiment, for example, the proximal end 452 may be attached to the handle assembly 200 by an internal channel retainer that is grounded to the handle assembly. However, other mechanical fastening arrangements could be employed. In one embodiment, the distal tube segment 410 is hollow or has a hose-receiving passage 416 therethrough. Likewise, the proximal tube segment 450 is hollow or has a hose-receiving passage 456 therethrough.

Figure 14:
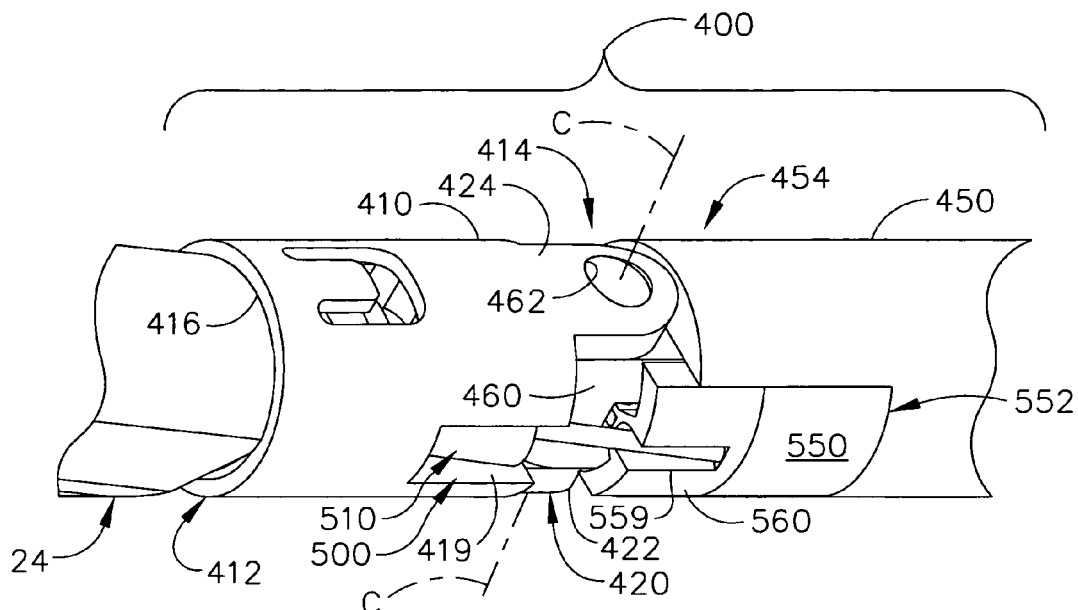
FIG. 14 is a partial perspective view of the articulation joint embodiment of the present invention.
Figure 15:
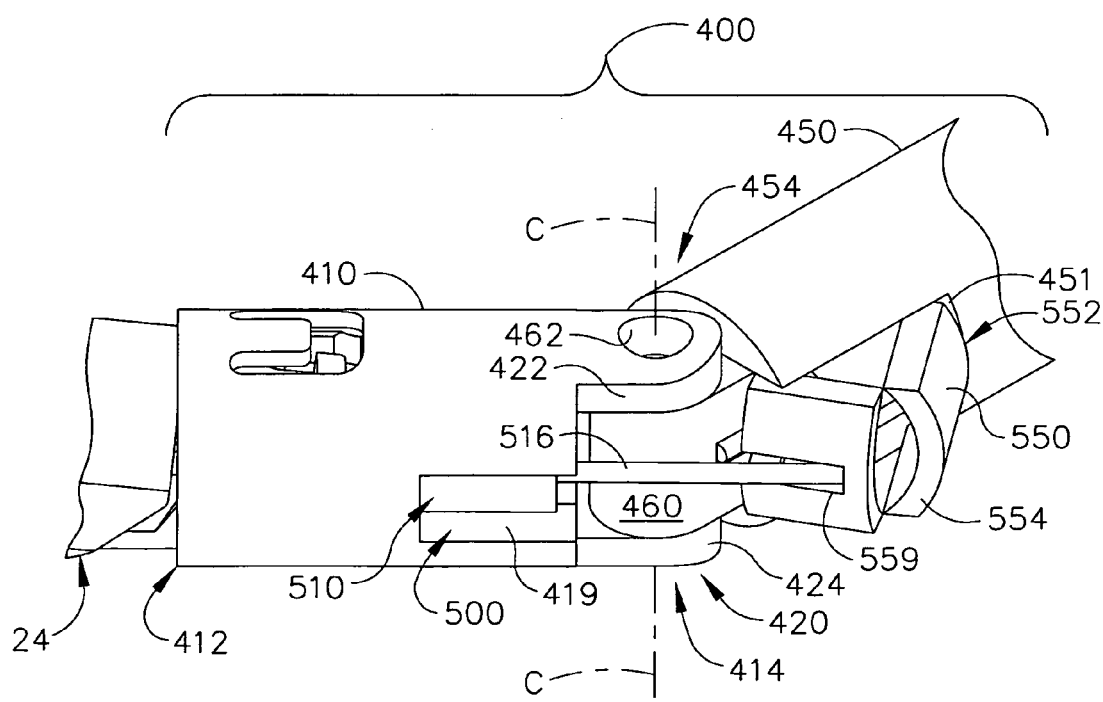
FIG. 15 is a partial perspective view of the articulation joint depicted in FIG. 14.

As can be seen in FIGS. 1, 14 and 15, the proximal end 414 of the distal tube segment 410 is pivotally coupled to the distal end 454 of the proximal tube segment 450 for pivotal travel about a pivot axis C-C between a position wherein the distal tube segment 410 is substantially coaxially aligned with the proximal tube segment 450 (i.e., wherein axes H-H and I-I are substantially coaxially aligned) and positions wherein they are not substantially coaxially aligned. In one non-limiting embodiment, for example, the proximal end 414 of the distal tube segment 410 has a yoke assembly 420 formed thereon that has first and second leg portions 422, 424. See FIG. 2. The distal end 454 of the proximal tube segment 450 has a tongue portion 460 protruding therefrom that is sized to be received between the legs 422, 424 of the yoke 420. A pin 462 extends through holes in the legs 422, 424 of the yoke 420 and the tongue 460 to pivotally couple the tongue 460 to the yoke 420 for pivotal travel about axis C-C. The pin 262 may be retained in the legs of the yoke by threads, glue, interference fit, etc. In other non-limiting embodiments, the pin 462 may have flanged ends. In one non-limiting embodiment, the tongue 460 is mechanically fastened within the distal end 454 of the proximal tube segment 450 by screws, pins, glue, etc.

When pivotally attached together as described above, the proximal and distal tube segments 410, 450 form a tube assembly 470 that has a passageway 472 or passageways for supporting the supply lines (collectively designated as 480) between the end effector 22 and the handle 200. It will be appreciated that the tube assembly 470 has a circumference "C" and shape such that when the distal tube 410 segment is coaxially aligned with the proximal tube segment 450, the tube assembly 470 may be inserted through the passageway 492 in a trocar 490. See FIG. 9. In one embodiment, the first and second tube segments 410, 450 have a round cross-sectional shape and are sized to be axially inserted through a round trocar passageway 492. The outer diameters of each the distal tube segments 410, 450 are less than the inner diameter of the trocar passageway 492 to facilitate axial insertion of the tube assembly 470 through the trocar passage 492 and, if desired or necessary, rotation of the tube assembly 470 within the trocar passageway 492. For example, if the trocar passageway 492 has an inner diameter of approximately 12.8 mm (0.503 inches), the maximum outer diameter of tube assembly 470 (and of each of the tube segments 410, 450) may be approximately 12.7 mm (0.500 inches). It is conceivable that, for applications wherein the ability to rotate the tube assembly 470 within the trocar passageway 492 is not necessary or desirable, trocars with passageways having non-circular cross-sections could be employed. In those cases, the tube assembly would have a cross-sectional shape that would facilitate axial insertion of the tube assembly through the trocar passageway and may closely resemble the cross-sectional shape of the trocar passageway. Thus, the various embodiments of the subject invention should not be limited to devices having a tube assembly with a round cross-sectional shape.

To facilitate pivotal manipulation of the surgical implement 12 relative to the proximal tube segment 450 after the surgical implement 12 and distal tube segment 410 have been inserted into the patient through the trocar passageway 492, an actuator assembly, generally designated as 500, is employed. In addition, to increase the pivotal forces generated by the actuator assembly 500, at least one, and preferably two pivotal, wall segments 550, 560 are provided to effectively lengthen the moment arm of the actuator assembly 500 after the joint assembly 400 has passed though the trocar passageway 492 into the patient.

Figure 12:
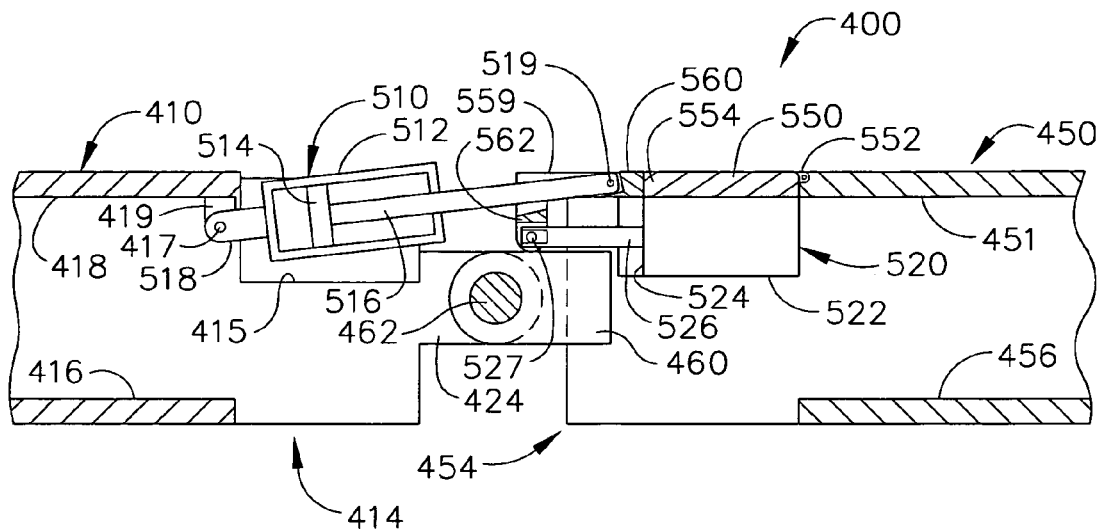
FIG. 12 is a partial cross-sectional view of one embodiment of an articulation joint of the present invention wherein the distal tube segment is substantially coaxially aligned with the proximal tube segment.
Figure 13:
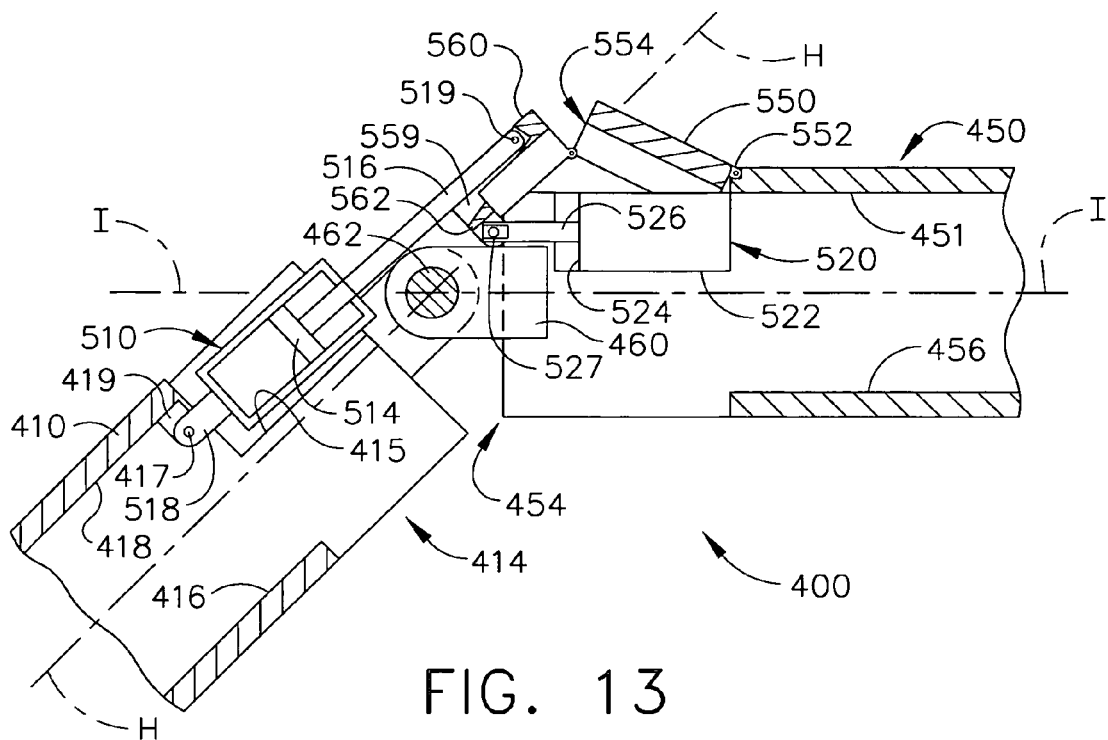
FIG. 13 is another partial cross-sectional view of the articulation joint of FIG. 12 wherein the distal tube segment is not substantially coaxially aligned with the proximal tube segment.

More particularly and with reference to FIGS. 12 and 13, one non-limiting embodiment of the present invention includes a first wall segment 550 that has a proximal end 552 pivotally attached to a remaining portion of the wall 451 of the proximal tube segment 450 for selective pivotal travel relative thereto. The opposite end 554 of the first wall segment 550 is pivotally attached to a second wall segment 560 for selective pivotal travel relative thereto. FIG. 12 illustrates the first and second wall segments 550, 560 in a first non-extended position wherein the wall segments 550, 560 do not extend outward beyond the desired circumferential boundary of the non-pivoting portions of the tube segments 410, 450. FIG. 13 illustrates the wall segments 550, 560 pivoted to a force generating position wherein the first and second wall segments 550, 560 extend outward beyond the circumferential boundary established by the non-pivoting portions of the first and second tube segments 410, 450.

As can be seen in FIGS. 12 and 13, in one non-limiting embodiment, first and second articulation cylinders 510, 520 are employed. First articulation cylinder 510 may comprise a conventional hydraulic or pneumatic cylinder that has a first housing 512 that contains a first piston 514 therein. A first piston rod or first actuation rod 516 is attached to the first piston 514 and protrudes out of the first housing 512. Movement of the piston 514 within the first housing 512 in response to the admission of pressurized fluid or air on one side or the other side of the piston 514 causes the first actuation rod 516 to be extended out of the first cylinder housing 512 or into the first cylinder housing 512. A distal end 518 of the first housing 512 is pivotally attached to a lug 419 attached to or formed in the wall 418 of the distal tube segment 410. The free end 519 of the first actuation rod 516 is pivotally attached to the second wall segment 560. To provide the requisite clearance for the first actuation rod 516 when the first and second wall segments 550 and 560 are in the non-extended position shown in FIG. 12, a slot 559 is provided in the second wall segment 550. Also, if necessary, a clearance pocket 415 may be provided in the proximal end 414 of the distal tube segment 410 to provide clearance for the first cylinder housing 512 to pivot about the pin 417 that affixes the first cylinder housing 512 to the lug 419. Thus, when in the non-extended position, no portion of the first articulation cylinder 510 protrudes outward from the outer circumference of the tube assembly 470 a distance that would cause any portion of the first articulation cylinder 510 to prevent or otherwise hinder axial insertion of the tube assembly 470 into the trocar passageway 492.

Also in this non-limiting embodiment, the second articulation cylinder 520 may comprise a conventional hydraulic or pneumatic cylinder that has a second housing 522 that contains a second piston 524 therein. A second piston rod or second actuation rod 526 is attached to the second piston 524 and protrudes out of the second housing 522. Movement of the second piston 524 within the second cylinder housing 522 in response to the admission of pressurized fluid or air on one side or the other side of the second piston 524 causes the actuation rod 526 to be extended out of the second cylinder housing 522 or into the second cylinder housing 522. The second cylinder housing 522 is mechanically attached to the proximal tube segment 450 by gluing, pinning, screwing etc. The free end 527 of the second actuation rod 526 is pivotally attached to a laterally extending lug 562 formed on the second wall segment 560.

Figure 12A:
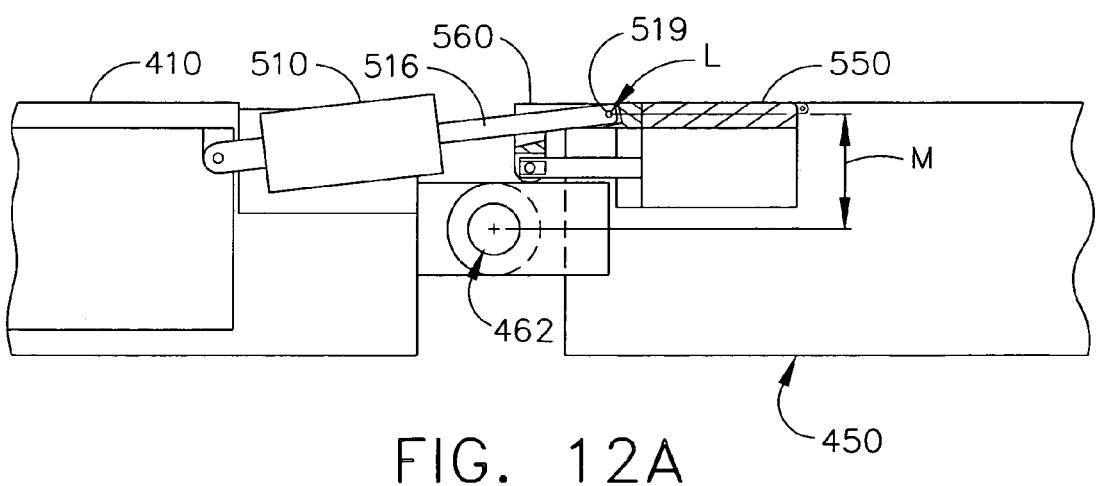
FIG. 12A is another partial cross-sectional view of the articulation joint embodiment of FIG. 12, with some of the element numbers omitted for clarity and to illustrate the actuator moment arm when the distal and proximal tube segments are substantially coaxially aligned.
Figure 13A:
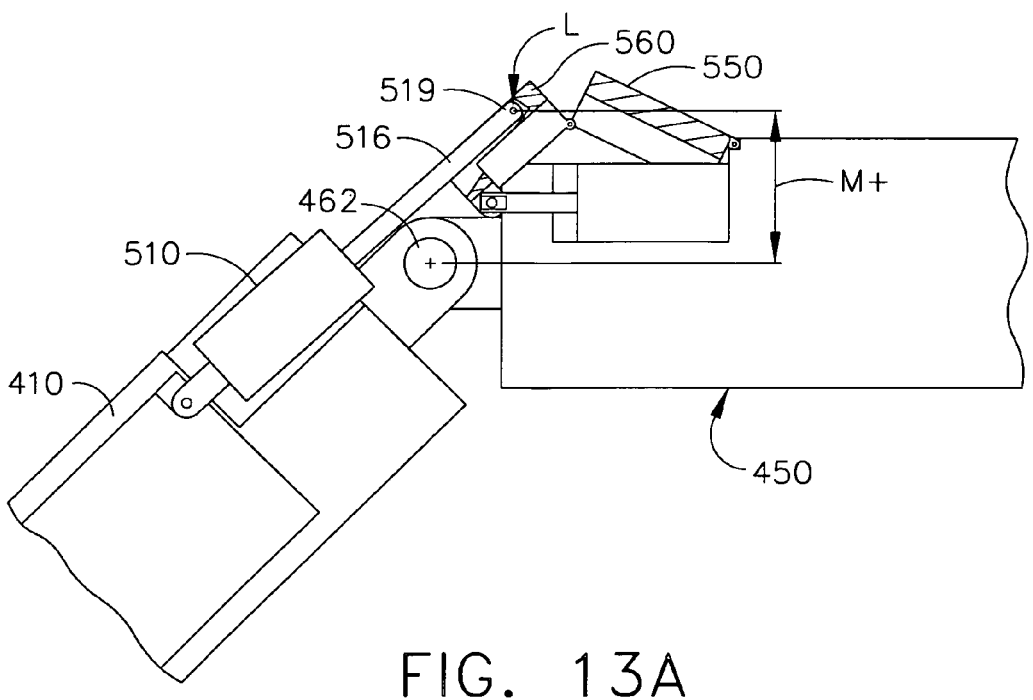
FIG. 13A is another partial cross-sectional view of the articulation joint embodiment of FIG. 12A, with some of the element numbers omitted for clarity and to illustrate the actuator moment arm when the distal and proximal tube segments are not substantially coaxially aligned.

Referring next to FIGS. 12A and 13A, the reader may acquire a better appreciation of the effectiveness of the various embodiments of the present invention. As can be seen in these Figures, the point wherein the end 519 of the first actuation rod 516 attaches to the second wall segment 560 is designated as point of attachment "L". Thus, when the distal tube segment 410 is in the unarticulated position (FIG. 12A), the moment arm created by the first actuator 510 is designated by the distance "M" between the point of attachment "L" and the center of the pivot pin 462. As can be seen in FIG. 13A, by pivoting the first and second wall segments 550, 560 out of axial alignment, the moment arm now has been increased to M+thereby increasing the amount of pivotal force generated to pivot the distal tube segment about the pivot pin 462.

The first and second articulation cylinders 510, 520 may be powered by the hydraulic system 210 or they may be powered by a separate hydraulic system. FIG. 11 depicts one method of controlling the first and second articulation cylinders 510, 520. As can be seen in that Figure, a supply line 570 is connected to the supply line 240 from the pump 230. A first portion 572 of the supply line 570 is attached to a first supply port in the first cylinder housing 512 for supplying pressurized fluid or air into the first cylinder housing 512 on one side of the first piston 514 and a second portion 574 of the supply line 570 is attached to a second supply port in the first housing 512 for supplying pressurized fluid or air into the first housing 512 on the other side of the first piston 514. A first supply valve 576 is mounted in the first portion 572 of the supply line 570 and a second supply valve 578 is mounted in the second portion 574 of the first supply line 570. An exhaust or return line 580 is provided to return the pressurized fluid from the first housing 512 to the fluid reservoir 232. The return line 580 has a first portion 582 and a second portion 584 attached to ports in the first housing 512. A first return valve 586 is mounted in the first portion 582 of the return line 580 and a second return valve 588 is mounted in the second portion 584 of the return line.

The supply line 570 further has a third portion 590 that is coupled to a third supply port in the second housing 522 on one side of the second piston 524 and the supply line 570 has a fourth portion 592 coupled to a fourth supply port in the second housing 522 on the other side of the second piston 524. A valve 596 is mounted in the third portion 590 and another valve 598 is mounted in fourth portion 592 of the supply line 570. Another return line 600 is provided to permit the pressurized fluid, air, etc. to return to the reservoir 232 from the housing 522 during actuation of the cylinder 520. The return line 600 has a third portion 602 attached to a third return port in the second housing 522 on one side of the second piston 524 and a fourth portion 604 of the return line 600 is coupled to a fourth return port in the second housing 522 on the other side of the second piston 524. A return valve 606 is provided in the third portion 602 of the return line 600 and another return valve 608 is provided in the portion 604 of the return line 600.

The valves may be controlled by the control circuit 300 or a second control circuit 300' of the type described above that may include a microprocessor and other related components including Random Access Memory (RAM), Read Only Memory (ROM), etc. In other non-limiting embodiments, the control circuit 300' may include various logical circuit elements. A conventional multiposition switch 610 may be connected to the second control circuit 300' for controlling the valves 576, 578, 586, 588, 594, 596, 606, 608.

FIG. 12 illustrates the joint assembly in a non-articulated position that would end able the tube assembly 470 to be inserted into the trocar. After the surgical implement 12 has be inserted through the trocar 490 and it becomes desirable to articulate the implement 12, the clinician activates the control circuit 300' through switch 610. Control circuit 300' activates pump 230 (if it has not already been activated) and supply valve 576 is opened to permit pressurized fluid or air to flow into the housing 512 to end the actuation rod 519 as shown in FIG. 13. Return valve 588 is opened to permit pressurized fluid on the opposite side of piston 514 to exit the housing through the return line 584. Likewise, valve 594 is opened to permit pressurized fluid to flow into the housing 522 on one side of the piston 524 and retract the actuation rod 526 to be retracted into the housing 522 as shown in FIG. 13. Return valve 608 is opened to permit pressurized fluid on the opposite side of the piston 524 to exit the housing 522. Such actuation of the articulation cylinders 510, 522 causes the first and second wall segments 550, 560 to pivot outward as shown in FIG. 13 to effectively increase the moment arm effect of the articulation cylinder 510 and thereby increase the articulation force generated thereby.

To return the first and second wall segments 550, 560 to their non-extended positions wherein they are substantially aligned with the remaining portions of the tube segments 410 and 450, the clinician moves the switch 610 to a position to signal the control circuit to close valves 576 and 588 for the first articulation cylinder 510 and open valves 578 and 586 to permit the piston 514 and actuation rod 516 to return to the position illustrated in FIG. 12. Likewise valves 594 and 608 are closed and valves 596 and 602 are opened to permit the piston 524 and actuation rod 526 to return to the position shown in FIG. 12. The hydraulic control system described above for actuating the articulation cylinders 510, 520, is but one example of a control system that may be used. The reader will appreciate that a variety of different control arrangements may be employed to activate the articulation cylinders without departing from the spirit and scope of the present invention. For example, the articulation cylinders 510, 520 as described above require the admission of pressurized fluid to move their respective pistons in both directions. Other cylinders that employ springs or other mechanisms for returning the pistons to a starting position may be employed along with appropriate valve and hydraulic fluid supply arrangement that are within the capabilities of the skilled artisan may be employed. It will be further appreciated that while the first and second wall segments 550, 560 as described herein are pivotally attached to the wall portion 451 of the proximal tube segment 450, in other embodiments, the first and second wall segments 550, 560 may be attached to the wall portion 418 of the distal tube segment 410 without departing from the spirit and scope of the present invention. Furthermore, while two pivotal wall segments have been illustrated, other embodiments of the present invention may employ only one pivoting wall segment or more than two pivoting wall segments.

Figure 16:
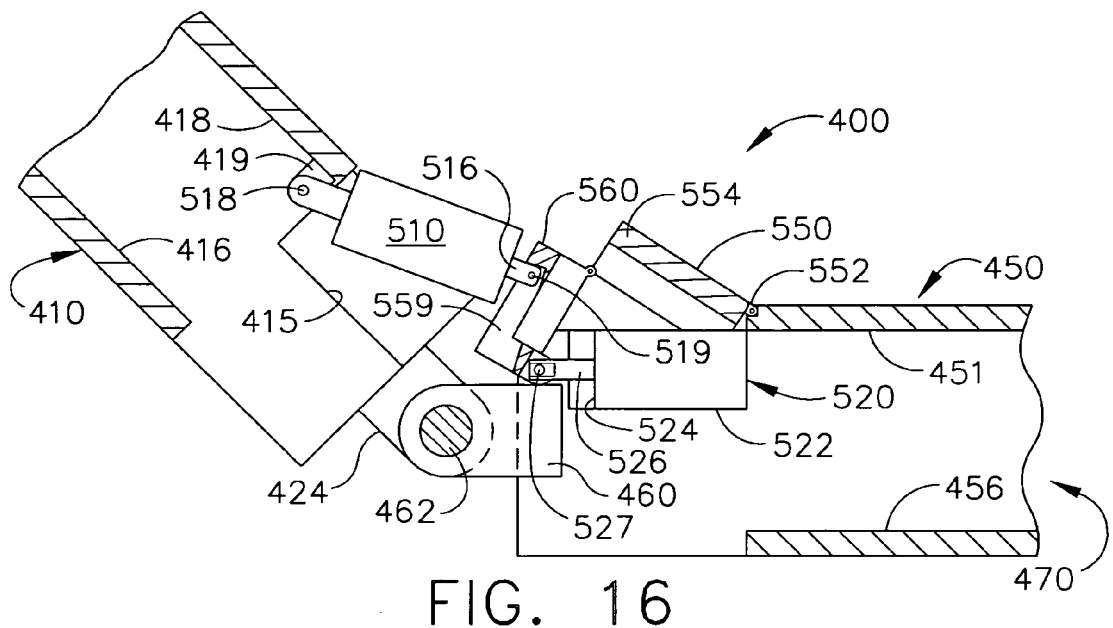
FIG. 16 is a partial cross-sectional view of another articulation joint of the present invention in an articulated position.

FIG. 16 illustrates a slightly different articulation cylinder arrangement for articulating the surgical implement 12 to the right side of the tube assembly 470. At least one version of this non-limiting embodiment would operate in the same manner described above.

Figure 17:
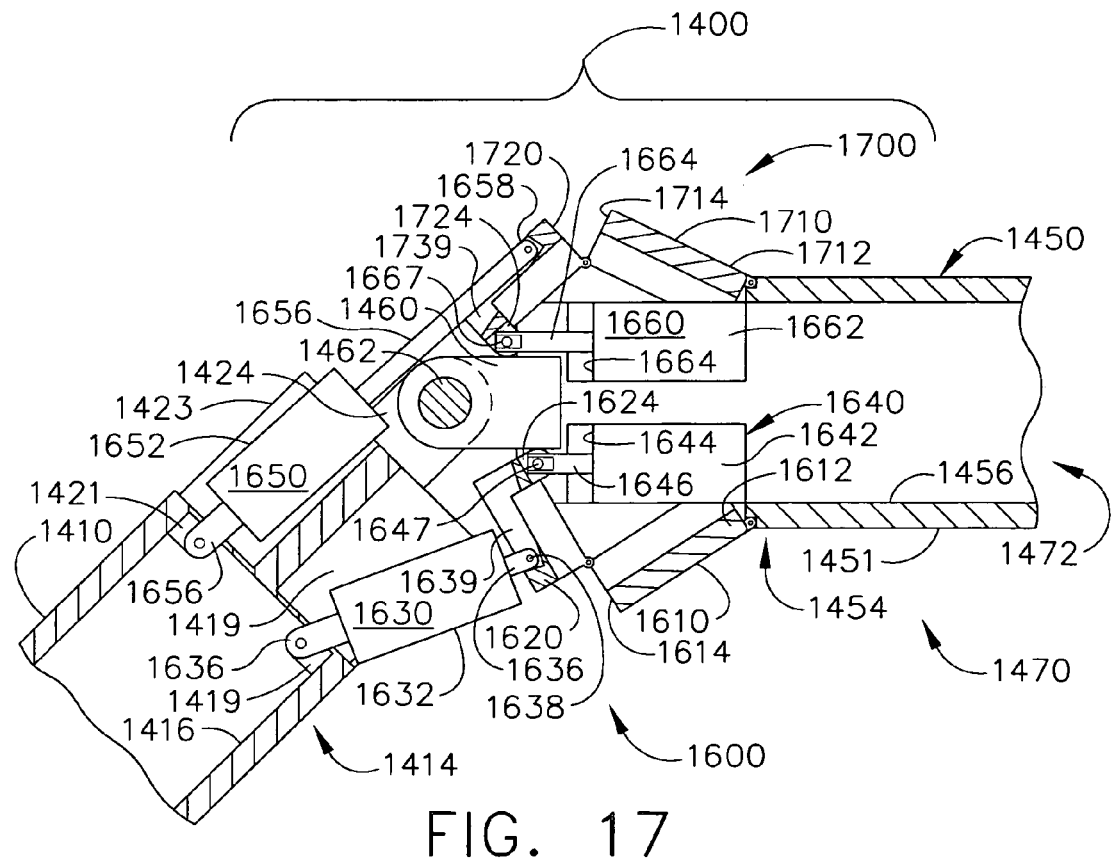
FIG. 17 is a partial cross-sectional view of another articulation joint of the present invention in an articulated position.

FIG. 17 illustrates a double articulation arrangement for articulating the surgical implement 12 to the left or right of the axis of the tube assembly 470. In the manner described above, the end effector 22 may be attached to the handle assembly 200 by an articulating joint assembly, generally designated as 1400. In one non-limiting embodiment, the articulating joint assembly 1400 includes a distal tube segment 1410 that has a distal end 1412 and a proximal end 1414. The distal end 1412 is mechanically coupled to the end effector body 24. Depending upon the anvil closure arrangement employed, the distal end 1412 may be non-movably attached to the end effector body or by a cable, flexible member or pivotable member. The joint assembly 1400 further includes a proximal tube segment 1450, that has a proximal end 1452 and a distal end 1454. The proximal end 1452 is mechanically attached to the handle assembly 200. In one embodiment, the distal tube segment 1410 is hollow or has a hose-receiving passage 1416 therethrough. Likewise, the proximal tube segment 1450 is hollow or has a hose-receiving passage 1456 therethrough.

The proximal end 1414 of the distal tube segment 1410 is pivotally coupled to the distal end 1454 of the proximal tube segment 1450 for pivotal travel about a pivot axis G-G. In one non-limiting embodiment, for example, the proximal end 1414 of the distal tube segment 1410 has a yoke assembly 1420 formed thereon that has first and second leg portions 1422, 1424. See FIG. 2. The distal end 1454 of the proximal tube segment 1450 has a tongue portion 1460 protruding therefrom that is sized to be received between the legs 1422, 1424 of the yoke 1420. A pin 1462 extends through holes in the legs 1422, 1424 of the yoke 1420 and the tongue 1460 to pivotally couple the tongue 1460 to the yoke 1420 for pivotal travel about axis G-G. The pin 1462 may be retained in the legs 1422, 1424 of the yoke 1420 by threads, glue, etc. In other non-limiting embodiments, the pin 1462 may have flanged ends. In one non-limiting embodiment, the tongue 1460 is mechanically fastened within the distal end 1454 of the proximal tube segment 1450 by screws, pins, glue, etc.

When pivotally attached together as described above, the proximal and distal tube segments 1410, 1450 form a tube assembly 1470 that has a passageway 1472 or passageways for supporting the supply lines (collectively designated as 480) between the end effector 22 and the handle 200. It will be appreciated that the tube assembly 1470 has a circumference "C" and shape such that when the distal tube 1410 segment is coaxially aligned with the proximal tube segment 1450, the tube assembly 1470 may be inserted through the passageway 492 in a trocar 490. In one embodiment, the first and second tube segments 1410, 1450 have a round cross-sectional shape and are sized to be axially inserted through a round trocar passageway 492. The outer diameters of each the distal tube segments 1410, 1450 are less than the inner diameter of the trocar passageway 492 to facilitate axial insertion of the tube assembly 1470 through the trocar passage 492 and, if desired or necessary, rotation of the tube assembly 1470 within the trocar passageway 492. For example, if the trocar passageway 492 has an inner diameter of approximately 12.8 mm (0.503 inches), the maximum outer diameter of tube assembly 1470 (and of each of the tube segments 410, 450) may be approximately 12.7 mm (0.500 inches). It is conceivable that, for applications wherein the ability to rotate the tube assembly 1470 within the trocar passageway 492 is not necessary or desirable, trocars with passageways having non-circular cross-sections could be employed. In those cases, the tube assembly would have a cross-sectional shape that would facilitate axial insertion of the tube assembly through the trocar passageway and may closely resemble the cross-sectional shape of the trocar passageway. Thus, the various embodiments of the subject invention should not be limited to devices having a tube assembly with a round cross-sectional shape.

Figure 18:
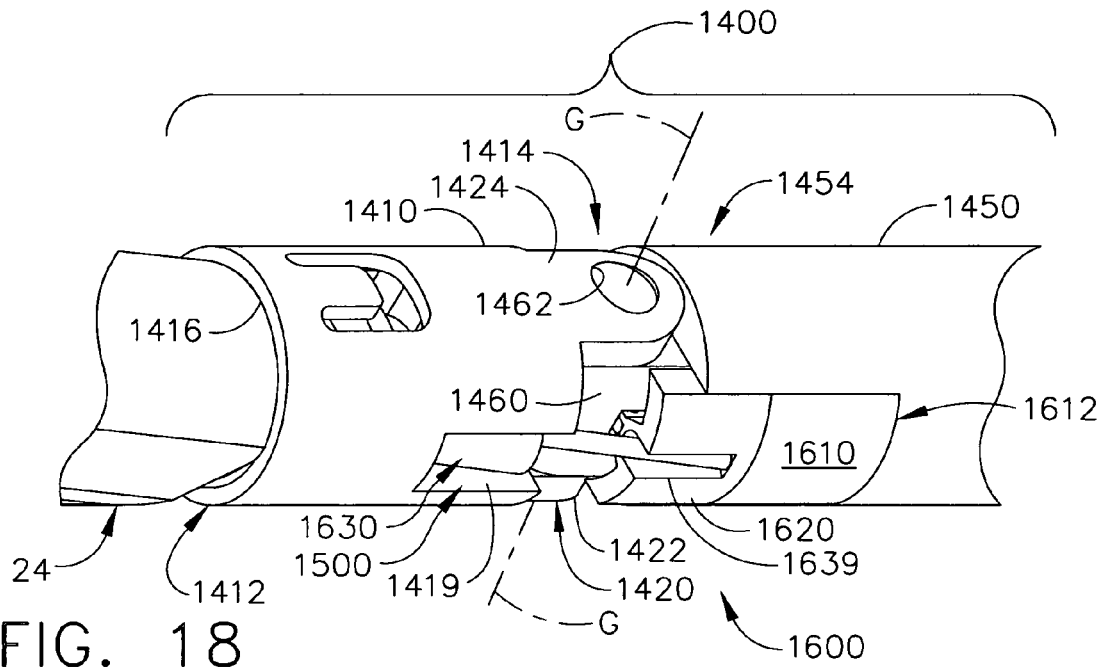
FIG. 18 is a partial perspective view of the articulation joint of FIG. 17 wherein the distal and proximal tube segments are substantially coaxially aligned.
Figure 19:
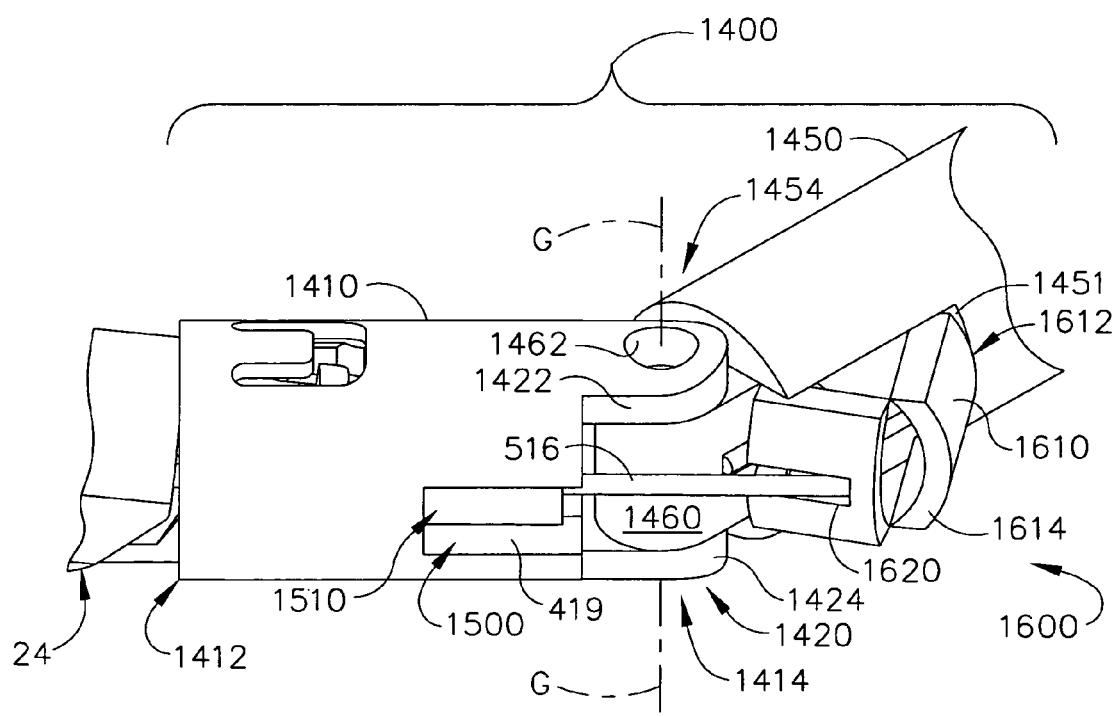
FIG. 19 is a partial perspective view of the articulation joint depicted in FIG. 17 in an articulated position.

To facilitate pivotal manipulation of the surgical implement 12 relative to the proximal tube segment 1450 after the surgical implement 12 and distal tube segment 1410 have been inserted into the patient through the trocar passageway 492, an actuator assembly, generally designated as 1500, is employed. This embodiment includes at least one left pivotal wall segment and at least one right pivotal wall segment. In the embodiment depicted in FIGS. 17 and 18, a left pair 1600 of wall segments 1610 and 1620 and a right pair 1700 of wall segments 1710 and 1720 are provided. The first left wall segment 1610 has a proximal end 1612 pivotally attached to a remaining portion of the wall 1451 of the proximal tube segment 1450 for selective pivotal travel relative thereto. The opposite end 1614 of the first left wall segment 1610 is pivotally attached to a second left wall segment 1620 for selective pivotal travel relative thereto. FIG. 18 illustrates the first and second left wall segments 1610, 1620 in a first non-extended position wherein the wall segments 1610, 1620 do not extend outward beyond the desired circumferential boundary of the non-pivoting portions of the tube segments 1410, 1450. FIG. 19 illustrates the wall segments 1610, 1620 pivoted to a force generating position wherein the first and second wall segments 1610, 1620 extend outward beyond the circumferential boundary established by the non-pivoting portions of the first and second tube segments 1410, 1450 such that the surgical implement 12 is articulated to the right relative to the axis of the tube assembly 1470.

Similarly, this embodiment also includes a pair 1700 of right wall segments 1710 and 1720. The first right wall segment 1710 has a proximal end 1712 pivotally attached to a remaining portion of the wall 1451 of the proximal tube segment 1450 for selective pivotal travel relative thereto. The opposite end 1714 of the first right wall segment 1710 is pivotally attached to a second right wall segment 1720 for selective pivotal travel relative thereto. Although not illustrated, the reader will understand that the first and second right wall segments 1710, 1720 are pivotable from a first non-extended position wherein the wall segments 1710, 1720 do not extend outward beyond the desired circumferential boundary of the non-pivoting portions of the tube segments 1410, 1450. FIG. 17 illustrates the wall segments 1710, 1720 pivoted to a force generating position wherein the first and second wall segments 1710, 1720 extend outward beyond the circumferential boundary established by the non-pivoting portions of the first and second tube segments 1410, 1450 such that the surgical implement 12 is articulated to the right relative to the axis of the tube assembly 1470.

As can be seen in FIG. 17 in one non-limiting embodiment, first and second left articulation cylinders 1630, 1640 and first and second right articulation cylinders 1650, 1660 are employed. First left articulation cylinder 1630 may comprise a conventional hydraulic or pneumatic cylinder that has a first housing 1632 that contains a piston (not shown) that has a first left piston rod or first left actuation rod 1634 attached thereto. Movement of the piston within the first housing 1632 in response to the admission of pressurized fluid or air on one side or the other side of the piston causes the first left actuation rod 1634 to be extended out of the first left cylinder housing 1632 and into the first left cylinder housing 1632. A distal end 1636 of the first left cylinder housing 1632 is pivotally attached to a lug 1419 attached to or formed in the wall 1418 of the distal tube segment 1410. The free end 1638 of the first left actuation rod 1634 is pivotally attached to the second left wall segment 1620. To provide the requisite clearance for the first left actuation rod 1634 when the first and second left wall segments 1610, 1620 are in the non-extended position shown in FIG. 18, a slot 1639 is provided in the second left wall segment 1620. Also, if necessary, a clearance pocket 1419 may be provided in the proximal end 1414 of the distal tube segment 1410 to provide clearance for the first left cylinder housing 1632 to pivot therein. Thus, when in the non-extended position, no portion of the first left articulation cylinder 1610 protrudes outward from the outer circumference of the tube assembly 1470 a distance that would cause any portion of the first left articulation cylinder 1610 to prevent or otherwise hinder axial insertion of the tube assembly 1470 into the trocar passageway 492.

Also in this non-limiting embodiment, the second left articulation cylinder 1640 may comprise a conventional hydraulic or pneumatic cylinder that has a second housing 1642 that contains a second left piston 1644 therein. A second left piston rod or second left actuation rod 1646 is attached to the second left piston 1644 and protrudes out of the second left cylinder housing 1644. Movement of the second left piston 1644 within the second left cylinder housing 1642 in response to the admission of pressurized fluid or air on one side or the other side of the second left piston 1644 causes the second left actuation rod 1646 to be extended out of the second left cylinder housing 1642 or into the second left cylinder housing 1642. The second left cylinder housing 1642 is mechanically attached to the proximal tube segment 1450 by gluing, pinning, screwing etc. The free end 1647 of the second left actuation rod 1646 is pivotally attached to a laterally extending lug 1624 formed on the second wall segment 1620.

Likewise, first right articulation cylinder 1650 may comprise a conventional hydraulic or pneumatic cylinder that has a first housing 1652 that contains a piston (not shown) that has a first left piston rod or first right actuation rod 1654 attached thereto. Movement of the piston within the first housing 1652 in response to the admission of pressurized fluid or air on one side or the other side of the piston causes the first right actuation rod 1654 to be extended out of the first right cylinder housing 1652 and into the first right cylinder housing 1652. A distal end 1656 of the first right cylinder housing 1652 is pivotally attached to a lug 1421 attached to or formed in the wall 1418 of the distal tube segment 1410. The free end 1658 of the first right actuation rod 1654 is pivotally attached to the second right wall segment 1720. To provide the requisite clearance for the first right actuation rod 1654 when the first and second right wall segments 1710, 1720 are in the non-extended position, a slot 1739 is provided in the second right wall segment 1720. Also, if necessary, a clearance pocket 1423 may be provided in the proximal end 1414 of the distal tube segment 1410 to provide clearance for the first right cylinder housing 1652 to pivot therein. Thus, when in the non-extended position, no portion of the first right articulation cylinder 1650 protrudes outward from the outer circumference of the tube assembly 1470 a distance that would cause any portion of the first right articulation cylinder 1650 to prevent or otherwise hinder axial insertion of the tube assembly 1470 into the trocar passageway 492.

Also in this non-limiting embodiment, the second right articulation cylinder 1660 may comprise a conventional hydraulic or pneumatic cylinder that has a second housing 1662 that contains a second right piston 1664 therein. A second right piston rod or second right actuation rod 1666 is attached to the second right piston 1664 and protrudes out of the second right cylinder housing 1662. Movement of the second right piston 1664 within the second right cylinder housing 1662 in response to the admission of pressurized fluid or air on one side or the other side of the second right piston 1664 causes the second right actuation rod 1666 to be extended out of the second right cylinder housing 1662 or into the second right cylinder housing 1662. The second right cylinder housing 1662 is mechanically attached to the proximal tube segment 1450 by gluing, pinning, screwing etc. The free end 1667 of the second right actuation rod 1666 is pivotally attached to a laterally extending lug 1724 formed on the second wall segment 1720.

Figure 20:
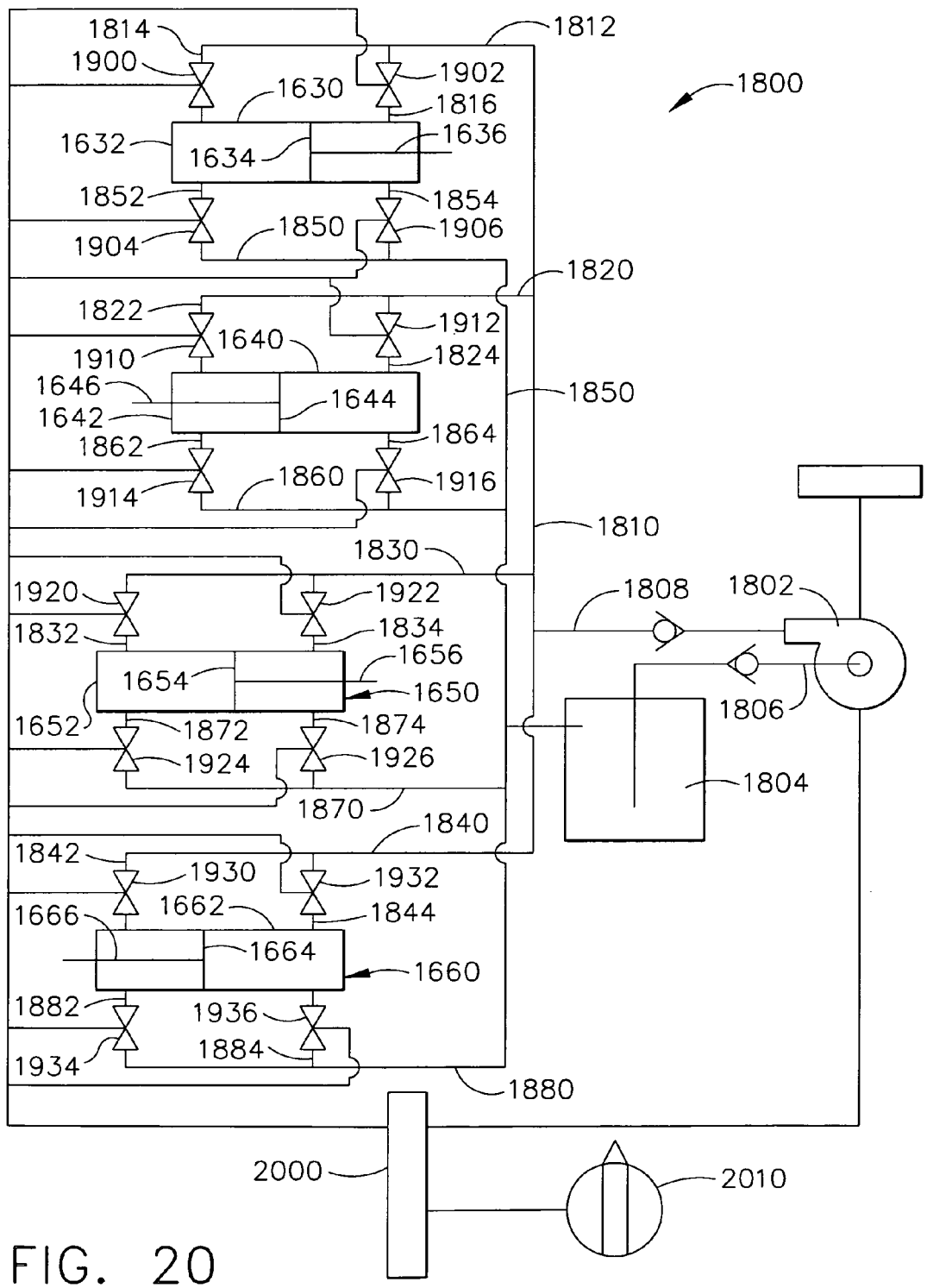
FIG. 20 is a schematic view of another hydraulic system embodiment that may be employed with various embodiments of the present invention.

The first and second left articulation cylinders 1630, 1640 and the first and second right articulation cylinders 1650, 1660 may be powered by the hydraulic system that powers the cutting and stapling features of the end effector 22 or they may be powered by a separate hydraulic system such as the one depicted in FIG. 20. As can be seen in that Figure, the system 1800 includes a pump 1802 that draws pressurized fluid or air from a reservoir 1804 through a supply line 1806. The discharge port of the pump 1802 discharges pressurized fluid through the line 1808 that is attached to a manifold line 1810. The manifold line 1810 is coupled to a first left supply line 1812 that has a first portion 1814 coupled to a port in the housing 1632 of the first left cylinder 1630 on one side of the piston 1634 thereof and a second portion 1816 coupled to another port in the housing 1632 on the other side of piston 1634. The manifold line 1810 is also coupled to a second left supply line 1820 that has a portion 1822 thereof coupled to a port in the housing 1642 of the second left articulation cylinder 1640 on one side of the piston 1644 and another portion 1824 of the supply line 1820 coupled to a port in the housing 1642 on another side of the piston 1644. The manifold line 1810 is further coupled to a third supply line 1830 that has a first portion 1832 coupled to a port in the housing 1652 of the first right articulation cylinder 1650 and another portion 1834 of the supply line 1830 coupled to another port in the housing 1652 of the first right articulation cylinder. The manifold line 1810 is also coupled to a fourth supply line 1840 that has a first portion 1842 coupled to a port in the housing 1662 of the second right articulation cylinder 1660 and a second portion 1844 of the fourth supply line 1840 is coupled to another port in the housing 1662 on the other side of piston 1654.

Also in this embodiment, a return line 1850 discharges into the reservoir 1804 and is coupled to a first return line 1852 that has a first portion 1854 coupled to a port in housing 1632 of the first left articulation cylinder 1630 on one side of the piston 1634 and also a second portion 1856 that is coupled to another port in housing 1632 on another side of the piston 1634. A second return line 1860 is coupled to the return line 1850 that has a first portion 1862 that is coupled a port in the housing 1642 of the second left articulation cylinder 1640 on one side of the piston 1644 and a second portion 1864 that is coupled to another port in the housing 1642 of the second left articulation cylinder 1640 on another side of the piston 1644. A third return line 1870 is coupled to the return line 1850 and has a first portion 1872 coupled to a port in housing 1652 of the first right articulation cylinder 1650 on one side of the piston 1654 and also a second portion 1874 that is coupled to another port in housing 1652 on another side of the piston 1654. A fourth return line 1880 is coupled to the return line 1850 that has a first portion 1882 that is coupled to a port in the housing 1662 of the second right articulation cylinder 1660 on one side of the piston 1664 and a second portion 1884 that is coupled to another port in the housing 1662 of the second right articulation cylinder 1660 on another side of the piston 1664.

To control the flow of pressurized fluid, air, etc. to the cylinders, a series of valves are employed. Valve 1900 is installed in the first portion 1814 of the supply line 1812 and valve 1902 is mounted in the second portion of the supply line 1812. Valve 1904 is mounted in the first portion 1852 of the return line 1850 and valve 1906 is mounted in the second portion 1854 of the return line 1850. Valve 1910 is installed in the first portion 1822 of the supply line 1820 and valve 1912 is installed in the second portion 1824 of the supply line 1820. Valve 1914 is installed in the first portion 1862 of the return line 1860 and valve 1916 is installed in the second portion 1864 of the return line 1860. Valve 1920 is installed in the first portion 1832 of the supply line 1830 and valve 1922 is installed in the second portion 1834 of the supply line 1830. Valve 1924 is installed in the first portion 1872 of the return line 1870 and valve 1926 is installed in the second portion 1874 of the return line 1870. Valve 1930 is installed in the first portion 1842 of the supply line 1840 and valve 1932 is installed in the second portion 1844 of the supply line 1840. Valve 1934 is installed in the first portion 1882 of the return line 1880 and valve 1936 is installed in the second portion 1884 of the return line 1880.

The valves may be controlled by the control circuit 3000 described above or by a second control circuit 2000 that may include a microprocessor and other related components including Random Access Memory (RAM), Read Only Memory (ROM), etc. In other non-limiting embodiments, the control circuit 2000 may include various logical circuit elements. A conventional multiposition switch 2010 may be connected to the second control circuit 2000 for controlling the valves 1900, 1902, 1904, 1906, 1910, 1912, 1914, 1916, 1920, 1922, 1924, 1926, 1930, 1932, 1934, 1936.

FIG. 18 illustrates the joint assembly 1400 in a non-articulated position that would enable the tube assembly 1470 to be inserted into the trocar. After the surgical implement 12 has be inserted through the trocar 490 and it becomes desirable to articulate the implement 12, the clinician activates the control circuit 2000 through switch 2010. Control circuit 2000 activates pump 1802 and supply valve 1902 is opened to permit pressurized fluid to flow into the housing 1632 of the first left articulation cylinder 1630 on one side of piston 1634 to retract the actuation rod 1636. Valve 1904 is opened to permit pressurized fluid on the opposite side of the piston 1634 to pass into the return line 1850 and valves 1900 and 1906 are closed. Valves 1910 and 1916 are opened and valves 1912 and 1914 are closed to permit the actuation rod 1646 of the second left articulation cylinder to be retracted. Valves 1920 and 1926 are open and valves 1922 and 1924 are closed to permit the actuation rod 1656 of the first right articulation cylinder 1650 to be extended. Valves 1930 and 1936 are open and valves 1932 and 1934 are closed to permit the actuation rod 1666 to be retracted. When the valves are in the aforementioned position, the tube segment 1410 (and the end effector 22 attached thereto) are pivoted to the left as shown in FIG. 17. After the desired procedure has been completed and the clinician desires to withdraw the instrument out through the trocar, the clinician activates the switch 2010 which signals the control circuit to open valves 1900, 1906, 1912, 1914, 1922, 1924, 1932, 1934 and close valves 1902, 1904, 1910, 1916, 1920, 1926, 1930, 1936.

The hydraulic control system 1800 described above for actuating the articulation cylinders 1630, 1640, 1650, 1660 is but one example of a control system that may be used. The reader will appreciate that a variety of different control arrangements may be employed to activate the articulation cylinders without departing from the spirit and scope of the present invention. For example, the articulation cylinders 1630, 1640, 1650, 1660 as described above each require the admission of pressurized fluid to move their respective pistons in both directions. Other cylinders that employ springs or other mechanisms for returning the pistons to a starting position may be employed along with appropriate valve and hydraulic fluid supply arrangements that are within the capabilities of the skilled artisan may also be employed.

Figure 21:
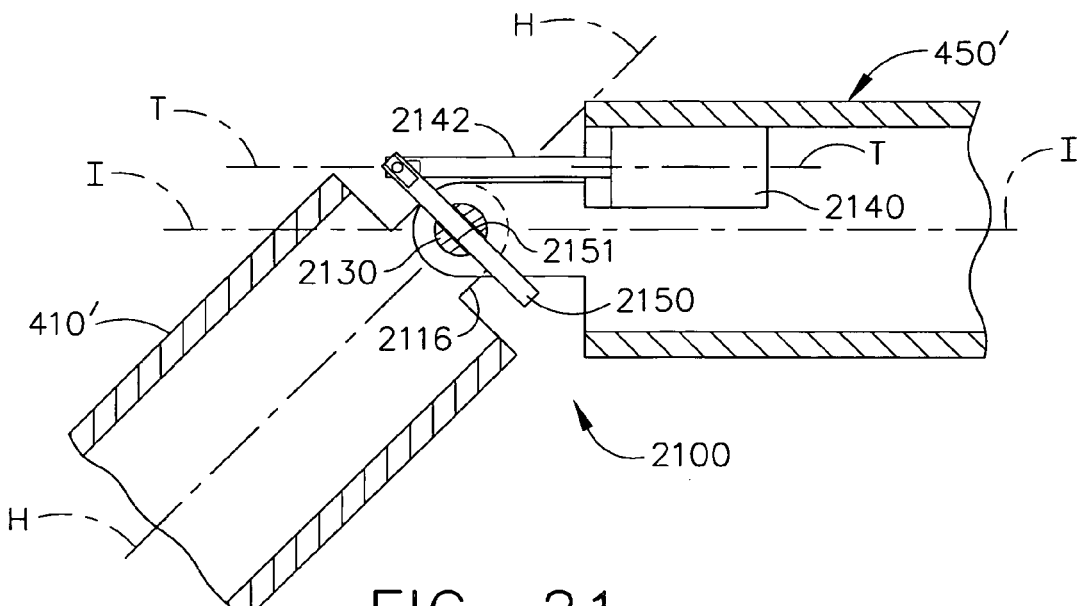
FIG. 21 is a partial cross-sectional view of another articulation joint embodiment of the present invention with the distal tube segment articulated relative to the proximal tube segment.
Figure 22:
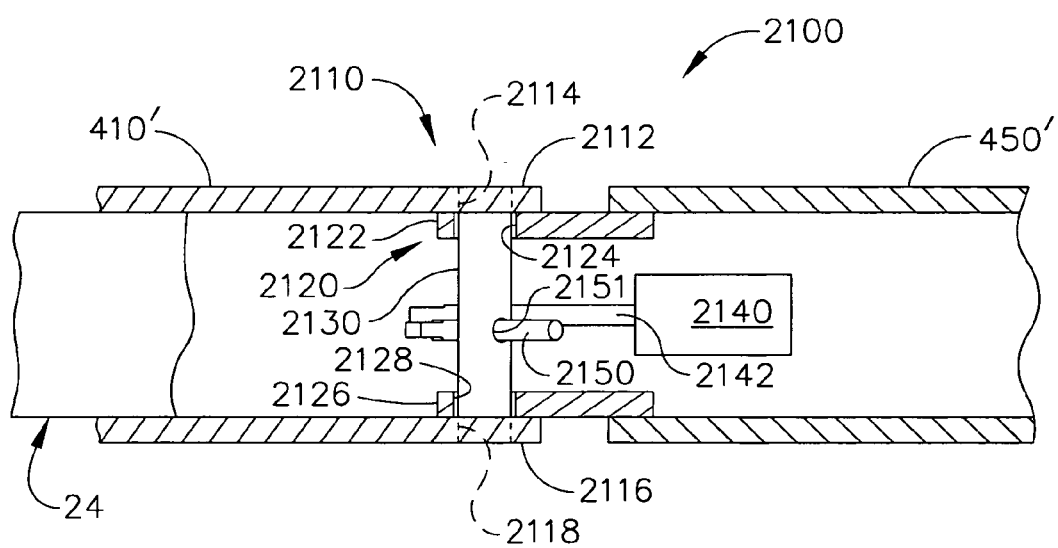
FIG. 22 is a partial cross-sectional view of the articulation joint of FIG. 21 with the distal tube segment and the proximal tube segment in coaxial alignment.

FIGS. 21 and 22 illustrate another embodiment of the present invention. As can be seen in these Figures, the distal tube segment 410' is attached to the proximal tube segment 450' by pivot pin and yoke arrangement designated as 2100. More specifically, as can be seen in these Figures, a first yoke assembly 2110 is formed on the proximal end of the distal tube segment 410'. The first yoke assembly 2110 has a first upper leg 2112 that has a first upper pin-receiving hole 2114 therein and a lower leg portion 2116 that is spaced from the upper leg portion 2112 and has a first lower pin receiving hole 2118 therethrough.

A second yoke assembly 2120 extends from the distal end of the proximal tube segment 450' and comprises a second upper leg portion 2122 that is either formed from or mechanically attached to the wall of the proximal tube segment 450' The second upper leg portion 2122 has a second upper pin-receiving hole 2124 therethrough. The second yoke assembly 2120 further includes a second lower leg portion 2126 that is either formed in or mechanically attached to the wall of the proximal tube segment 450'. The second lower leg portion has a second lower pin-receiving hole 2128 therethrough. The pin-receiving holes 2114, 2118, 2124, 2128 are coaxially aligned to receive a pivot pin 2130 therethrough. Pivot pin 2130 is non-movably attached to the first upper leg 2112 and the first lower leg 2116 and is otherwise free to rotate within the second upper pin-receiving hole 2124 and the second lower pin-receiving hole 2128 in the second upper leg 2122 and second lower leg 2126, respectively. Thus, rotation of pin 2130 within the holes 2124, 2128 causes the distal tube segment 410' to pivot relative to the proximal tube segment 450'.

To facilitate pivotal rotation of pin 2130 and distal tube segment 410', an actuator 2140 is supported within the proximal tube segment 450'. In one embodiment, the actuator 2140 comprises a hydraulic cylinder that may be controlled by a hydraulic system arrangement described above. The hydraulic cylinder 2140 has an extendable and retractable actuation rod 2142 therein. In one embodiment, the actuation rod 2142 has an axis T-T that is substantially parallel to the axes H-H and I-I of the distal and proximal tube segments 410', 450', when those axes H-H- and I-I are coaxially aligned. As can also be seen in FIGS. 21 and 22, a moment rod 2150 is pivotally attached to the end of the actuation rod 2142 and slidably extends through an opening 2151 in the pin 2130. Thus, when the actuation rod 2142 is extended, the moment arm created between the center point of the pin 2130 and the end of the actuation rod 2142 increases and thereby increases the amount of pivot force generated to cause the moment rod 2150 to slide within the opening 2151 in the pivot pin 2130 and cause the pivot the pin 2130 and the distal tube segment 410 attached thereto to pivot. To bring the distal tube segment 410' into axial alignment with the proximal tube segment 450' the actuation rod 2142 is retracted and the moment arm 2150 slides within the opening 2151 in the pin 2130 and causes the pin 2130 to pivot in an opposite direction. Those of ordinary skill in the art will understand that the cylinder 2140 could be located within the proximal tube segment such that actuation of the actuation rod 2142 in the above-describe manner causes the distal tube segment to pivot to the right.

The various non-limiting embodiments of the present invention provide a host of advantages over prior art articulated surgical instruments. In particular, the various embodiments of the subject invention enable the portions of the tube member that attach a surgical implement to a handle to be inserted through a trocar or similar device and then be selectively articulated within the patient. The various articulating joint and actuator arrangements are capable of generating higher pivoting forces by increasing the length of the moment arm between the actuator and the pivot axis or point. While the various embodiments have been described herein in connection with use with a hydraulically operated endocutter, those of ordinary skill in the art would appreciate that the various embodiments of the subject invention could be employed with electrically powered endocutters and with a host of other types of surgical implements, regardless of whether they are electrically or hydraulically powered.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures.

What is claimed is:

1. A surgical instrument, comprising:
   a handle assembly;
   an elongated tube assembly coupled to said handle assembly, said elongated tube assembly comprising:
      a proximal tube segment attached to said handle assembly, said proximal hollow tube segment having a proximal wall; and
      a distal tube segment pivotally attached to said proximal tube segment and being selectively pivotable between a position wherein said distal tube segment is in substantial axial alignment with said proximal tube segment and positions wherein said distal tube segment is not substantially axially aligned with said proximal tube segment, said distal tube segment having a distal wall;
   an actuator assembly supported by at least one of said proximal and distal tube segments and being coupled to at least one portion of one of said proximal and distal walls such that, upon actuation of said actuator assembly, said portion of one of said proximal and distal walls is pivoted out of substantial axial alignment with a corresponding portion of one of said proximal and distal walls to cause said distal tube segment to articulate out of substantial axial alignment with said proximal tube segment; and
   a surgical implement attached to said distal tube segment;
   wherein said at least one portion of one of said proximal and distal walls comprises:
      a first wall segment pivotally coupled to a remaining portion of said proximal wall and being selectively pivotable between a position wherein said first wall segment is substantially axially aligned with said remaining portion of said proximal wall and positions wherein said first wall segment is not substantially axially aligned with said remaining portion of said proximal wall;
      a second wall segment pivotally coupled to said first wall segment and being attached to said actuator assembly, said second wall segment being selectively pivotable between another position wherein said second wall segment is substantially, axially aligned with said first wall segment and said remaining portion of said proximal wall and other positions wherein said second wall segment is not substantially axially aligned with said first wall segment;
      a third wall segment pivotally coupled to another portion of said remaining portion of said proximal wall and being selectively pivotable between a position wherein said third wall segment is substantially axially aligned with said another portion of said remaining portion of said proximal wall and positions wherein said third wall segment is not substantially axially aligned with said another portion of said remaining portion of said proximal wall; and
      a fourth wall segment pivotally coupled to said third wall segment and being attached to said actuator assembly, said fourth wall segment being selectively pivotable between a third position wherein said fourth wall segment is substantially axially aligned with said third wall segment and said another portion of said remaining portion of said proximal wall and other positions wherein said fourth wall segment is not substantially axially aligned with said third wall segment.

2. The surgical instrument of claim 1 wherein said actuator assembly comprises:
   a first actuator supported by said distal tube segment and attached to said second wall segment;
   a second actuator supported by said proximal tube segment and attached to said second wall segment;
   a third actuator supported by said distal tube and attached to said fourth wall segment;
   a fourth actuator supported by said proximal tube and attached to another portion of said fourth wall segment.

3. The surgical instrument of claim 2 wherein said first, second, third and fourth actuators comprise first, second, third, and fourth hydraulic cylinders, respectively.

4. The surgical instrument of claim 3 wherein said first hydraulic cylinder comprises:

a first cylinder housing supported by said distal tube segment, said first cylinder housing movably supporting a first piston therein; and a first actuator rod extending from said first housing and being selectively extendable and retractable relative thereto in response to movement of said first piston within said first housing, said first actuator rod attached to a portion of said second wall segment and wherein said second hydraulic cylinder comprises:

a second cylinder housing supported by said proximal tube segment, said second cylinder housing movably supporting a second piston therein; and a second actuator rod extending from said second housing and being selectively extendable and retractable relative thereto in response to movement of said second piston within said second housing, said second actuator rod attached to another portion of said second wall segment and wherein said third hydraulic cylinder comprises:

a third cylinder housing supported by said distal tube segment, said third cylinder housing movably supporting a third piston therein; and a third actuator rod extending from said third housing and being selectively extendable and retractable relative thereto in response to movement of said third piston within said third housing, said third actuator rod attached to a portion of said fourth wall segment and wherein said fourth hydraulic cylinder comprises:

a fourth cylinder housing supported by said proximal tube segment, said fourth cylinder housing movably supporting a fourth piston therein; and a fourth actuator rod extending from said fourth housing and being selectively extendable and retractable relative thereto in response to movement of said fourth piston within said fourth housing, said fourth actuator rod attached to another portion of said fourth wall segment.

\* \* \* \* \*